(12) United States Patent
Goetz

(10) Patent No.: US 9,723,987 B2
(45) Date of Patent: Aug. 8, 2017

(54) REMOTE CALIBRATION OF AN IMPLANTABLE PATIENT SENSOR

(75) Inventor: Steven M. Goetz, North Oaks, MN (US)

(73) Assignee: Medtronic, Inc., Minneapolis, MN (US)

(*) Notice: Subject to any disclaimer, the term of this patent is extended or adjusted under 35 U.S.C. 154(b) by 388 days.

(21) Appl. No.: 12/738,047

(22) PCT Filed: Sep. 29, 2008

(86) PCT No.: PCT/US2008/078125
§ 371 (c)(1),
(2), (4) Date: Apr. 14, 2010

(87) PCT Pub. No.: WO2009/055205
PCT Pub. Date: Apr. 30, 2009

(65) Prior Publication Data
US 2010/0223020 A1    Sep. 2, 2010

Related U.S. Application Data

(60) Provisional application No. 61/000,285, filed on Oct. 24, 2007.

(51) Int. Cl.
*A61B 5/00* (2006.01)
*A61B 5/11* (2006.01)
*G06F 19/00* (2011.01)

(52) U.S. Cl.
CPC .......... *A61B 5/0031* (2013.01); *A61B 5/0022* (2013.01); *A61B 5/11* (2013.01);
(Continued)

(58) Field of Classification Search
CPC ..... A61B 5/1116; A61B 5/1118; A61B 6/582; G06F 19/3412
(Continued)

(56) References Cited

U.S. PATENT DOCUMENTS 5,593,431 A * 1/1997 Sheldon .......................... 607/19
5,620,473 A * 4/1997 Poore ................. A61N 1/37252
607/27

(Continued)

FOREIGN PATENT DOCUMENTS

EP    1491234    12/2004
WO    WO96/22125    7/1996
(Continued)

OTHER PUBLICATIONS

PCT/US08/78134: Search Report and Written Opinion dated Jun. 9, 2009.
(Continued)

*Primary Examiner* — Gregory J Toatley
*Assistant Examiner* — Michael Dalbo
(74) *Attorney, Agent, or Firm* — Shumaker & Sieffert, P.A.

(57) ABSTRACT

Techniques for remotely calibrating an implanted patient sensor with a remote networking device are described. In some embodiments, the sensor is a component of an implantable medical device (IMD). The remote networking device communicates with the IMD via a network to which the IMD and/or external programmer is connected. The IMD may transmit sensor information to the remote networking device when the IMD detects a problem with the sensor or when the patient indicates that therapy is not correctly selected for different activities. New calibration settings may be remotely generated by directly interrogating the sensor and/or communicating with the patient in order to associate sensor output with patient activities, motions, or postures.

38 Claims, 13 Drawing Sheets

(52) U.S. Cl.
CPC .............. *A61B 2560/0223* (2013.01); *A61B 2560/0271* (2013.01); *A61B 2562/0219* (2013.01); *G06F 19/3418* (2013.01)

(58) Field of Classification Search
USPC ...................................... 702/104; 607/6, 19
See application file for complete search history.

(56) References Cited

U.S. PATENT DOCUMENTS

| | | | |
|---|---|---|---|
| 5,752,976 A * | 5/1998 | Duffin et al. ................ | 607/32 |
| 6,044,294 A * | 3/2000 | Mortazavi et al. ........... | 600/547 |
| 6,044,297 A | 3/2000 | Sheldon et al. | |
| 6,662,052 B1 | 12/2003 | Sarwal et al. | |
| 6,993,379 B1 * | 1/2006 | Kroll ................. | A61B 5/04021 600/509 |
| 7,221,263 B2 * | 5/2007 | Moore et al. ................ | 340/427 |
| 7,273,457 B2 * | 9/2007 | Penner .......................... | 600/561 |
| 2001/0031997 A1 | 10/2001 | Lee | |
| 2002/0029002 A1 | 3/2002 | Bardy | |
| 2002/0143372 A1 | 10/2002 | Snell et al. | |
| 2002/0183693 A1 | 12/2002 | Peterson et al. | |
| 2006/0089592 A1 | 4/2006 | Kadhiresan et al. | |
| 2006/0235289 A1 * | 10/2006 | Wesselink et al. .......... | 600/407 |
| 2007/0142868 A1 | 6/2007 | Moon et al. | |

FOREIGN PATENT DOCUMENTS

| | | |
|---|---|---|
| WO | WO2004/067083 | 8/2004 |
| WO | WO2004/093989 | 11/2004 |
| WO | WO2006/099035 | 9/2006 |
| WO | WO2007/079543 | 7/2007 |
| WO | WO2007/112092 | 10/2007 |
| WO | WO2009/055202 | 4/2009 |
| WO | WO2009/055204 | 4/2009 |
| WO | WO2009/055205 | 4/2009 |
| WO | WO2009/055206 | 4/2009 |
| WO | WO2009/055207 | 4/2009 |

OTHER PUBLICATIONS

PCT/US08/78134: Response to Written Opinion filed Sep. 9, 2009.
PCT/US08/78134: $2^{nd}$ Written Opinion dated Feb. 5, 2010.
PCT/US08/78134: Response to $2^{nd}$ Written Opinion dated Apr. 5, 2010.
PCT/US08/78134: IPRP dated Apr. 22, 2010.
PCT/US08/78099: Search Report and Written Opinion dated Dec. 11, 2008.
PCT/US08/78099: Response to Written Opinion dated Aug. 14, 2009.
PCT/US08/78099: IPRP dated Feb. 2, 2010.
PCT/US08/78125: Search Report and Written Opinion dated Feb. 2, 2009.
PCT/US08/78114: Search Report and Written Opinion dated Feb. 10, 2009.
PCT/US08/78114: Response to Written Opinion dated Aug. 21, 2009.
PCT/US08/78114: IPRP dated Dec. 18, 2009.
PCT/US08/78127: Search Report and Written Opinion dated Dec. 12, 2008.
PCT/US08/78127: Response to Written Opinion dated Jun. 12, 2009.
PCT/US08/78127: IPRP dated Dec. 21, 2009.

* cited by examiner

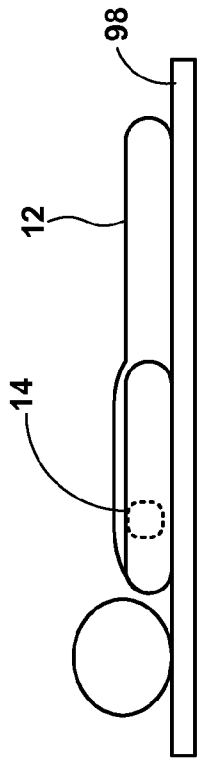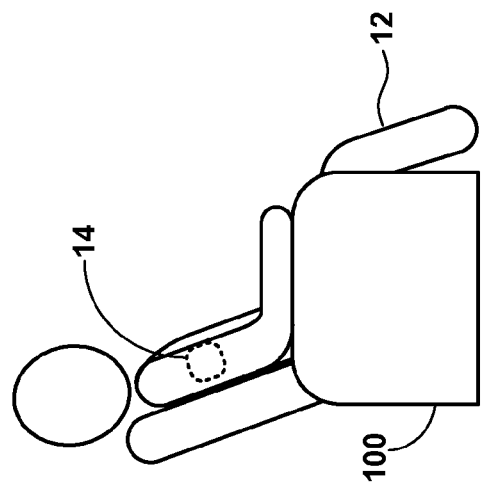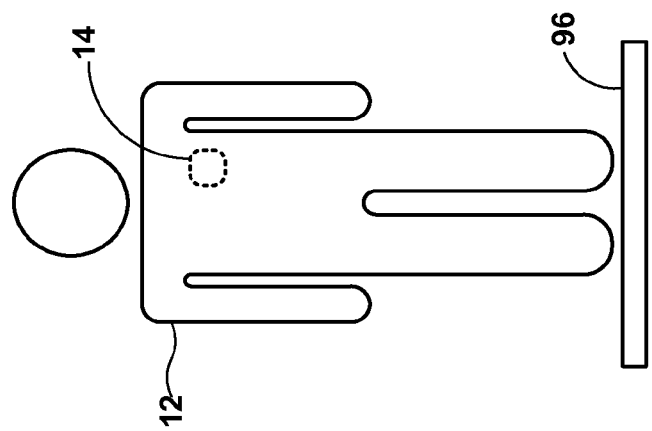

REMOTE CALIBRATION OF AN IMPLANTABLE PATIENT SENSOR

This application is a U.S. National Stage filing under 35 U.S.C. 371 of copending PCT Application Serial No. PCT/US2008/078125, filed Sep. 29, 2008, which claims priority to U.S. Provisional Application No. 61/000,285, filed Oct. 24, 2007, entitled "Calibration of an Implantable Patient Sensor," the disclosures of each of the above which are incorporated by reference as if re-written herein in their entirety.

TECHNICAL FIELD

The invention relates to medical devices and, more particularly, to medical devices comprising sensors.

BACKGROUND

There are a number of situations in which it may be desirable to monitor a patient via one or more sensors. For example, it may be desirable to monitor the progression of an ailment or symptoms of the patient via one or more sensors. As another example, the efficacy of a treatment delivered to the patient may be monitored via one or more sensors. Furthermore, a medical device may control delivery of a therapy, e.g., provide closed-loop therapy, based on signals from one or more patient sensors.

In some cases, as an example, an ailment may affect a patient's activity level or range of activities by preventing the patient from being active. For example, chronic pain may cause a patient to avoid particular physical activities, or physical activity in general, where such activities increase the pain experienced by the patient. When a patient is inactive, he or she may be more likely to be recumbent, i.e., lying down, or sitting, and may change postures less frequently. Other ailments that may affect patient activity include movement disorders such as tremor, Parkinson's disease, multiple sclerosis, epilepsy, spasticity, or other neurological disorders, such as psychological or mood disorders, which may result in irregular movement or activity, or a generally decreased level of activity. In such cases, it may be desirable to monitor the patient with one or more sensors that generate a signal as a function of patient activity, motion, and/or posture.

In some cases, these ailments are treated via a medical device, such as an implantable medical device (IMD). For example, patients may receive an implantable neurostimulator or drug delivery device to treat chronic pain, a movement disorder, or a psychological disorder. The IMD, or some other system component in communication with the IMD, may collect objective data based on signals generated by one or more sensors. The IMD, other system component, patient, or a clinician may use the sensor data to, for example, evaluate symptom progression or therapy efficacy, optimize the therapy, or provide closed-loop feedback control of the therapy.

Other example situations in which patient sensors may be used to provide feedback for controlling the delivery of a therapy to a patient by an IMD are spinal cord stimulation and cardiac pacing. In the case of spinal cord stimulation, an activity, motion, or posture sensor may be used to control the intensity, e.g., amplitude or rate, of the electrical stimulation delivered to the spinal cord to alleviate pain. Adjusting the stimulation intensity in this manner may compensate for activity-dependent or posture-dependent changes in pain intensity or location, which may in by due, in part, to changes in the position of electrodes relative to the spinal cord. In the case of cardiac pacing, the rate of pacing may be adjusted as a function of patient demand. Patient demand may be indicated by, for example, patient activity, motion, or posture.

One example of a sensor capable of detecting patient posture, motion, and activity is an accelerometer, such as a multi-axis accelerometer. A three-axis accelerometer, for example, may be able to detect motion and posture by detecting acceleration along three axes. Another example of a sensor capable of detecting posture, motion, or activity is a mercury switch sensor, an example of which is described in commonly-assigned U.S. Pat. No. 5,031,618, to Mullett.

Generally, a clinician uses a programmer, e.g., a computing device capable of communicating with implantable medical devices via local device telemetry, to program an implantable medical device for delivery of therapy to a patient. In some cases, such clinician programmers take the form of handheld and/or tablet-type computing devices. Handheld and/or tablet-type clinician programmers can allow for a more natural "bedside" interaction between clinicians and patients during the programming process. Handheld and/or tablet-type clinician programmers can also allow the programmer to be handed off to the patient for entry of symptom, therapy efficacy, or other patient data.

SUMMARY

In general, the disclosure is directed to remotely calibrating an implantable patient sensor through the use of a remote networking device. In some embodiments, the sensor is a component of an implantable medical device (IMD). The sensor may be an activity, motion and/or posture sensor, i.e., may generate a signal as a function of one or more of the activity, motion, or posture of the patient in which the sensor is implanted. For example, the sensor may be a multi-axis accelerometer.

In some embodiments, an IMD may utilize such a sensor for control or evaluation of therapy. At some point after implantation, it is possible that the sensor output may no longer be effective for these or other purposes because of a change in orientation of the sensor or IMD within the patient, e.g. flipped within the patient, changes to the posture or activity being sensed, electronic drift, or some other change to the sensor. The IMD, the patient, or some other component of a system comprising may initiate a performance check of the sensor output to determine if there is any problem with the sensor. The performance check may include transmitting sensor information, which may comprise a signal generated by the sensor, to a remote networking device via a network. In this manner, the patient need not visit the clinician in person in order to troubleshoot potential problems with the sensor.

The remote networking device may communicate with the IMD, an external programmer for the IMD, or some other component of an IMD system, via a network. In some embodiments, the IMD may transmit sensor information to the remote networking device for review by a clinician. The clinician may remotely generate new calibration settings for the sensor by directly interrogating the sensor and/or communicating with the patient in order to associate activity sensor output with patient activity, motion, or posture. In other embodiments, a remote networking device or server may generate new calibration settings, which may be reviewed by a clinician prior to transmittal to the IMD. In some examples, the new calibration settings may be generated by the IMD and/or the external programmer and reviewed or confirmed by the clinician.

In one embodiment, the invention provides a method comprising receiving a signal generated by an implantable sensor at a remote networking device via a network, wherein the implantable sensor generates the signal as a function of at least one of activity, motion, or posture of a patient, and calibrating the implantable sensor via the remote networking device based on the sensor signal.

In another embodiment, the invention provides a remote networking device comprising a communications circuit that receives a signal generated by an implantable sensor via a network, wherein the signal is generated by the implantable sensor as a function of at least one of activity, motion, or posture of a patient, and a processor that calibrates the sensor via the network based on the signal.

In another embodiment, the invention provides a method comprising identifying possible miscalibration of an implantable sensor that generates a signal as a function of at least one of activity, motion, or posture of a patient, transmitting the signal generated by the sensor to a remote networking device via a network in response to the identification, and receiving a calibration setting for the sensor from the remote networking device via the network in response to the signal.

In another embodiment, the invention provides a communications circuit, and a processor. The processor identifies possible miscalibration of an implantable sensor that generates a signal as a function of at least one of activity, motion, or posture of a patient, transmits the signal to a remote networking device via the communications circuit and a network in response to the identification, and receives a calibration setting for the sensor from the remote networking device via the communications circuit and the network in response to the signal.

In another embodiment, the invention provides a system comprising a local device and a remote networking device. The local device that identifies possible miscalibration of an implantable sensor that generates a signal as a function of at least one of activity, motion, or posture of a patient, transmits the signal in response to the identification, and receives a calibration setting for the sensor in response to the signal. The remote networking device communicates with the local device via a network, wherein the remote networking device receives the signal from the local device via the network, and transmits a sensor calibration setting to the local device in response to the signal.

The invention is capable of providing one or more advantages. For example, an implantable sensor may be remotely recalibrated, thereby avoiding the need for the patient to visit a clinician's office. In this manner, remote calibration may reduce costs associated with additional patient visits to the clinician's office and time associated with each appointment. In addition, where the sensor is used for control of therapy, remote calibration may reduce the amount of time that the patient may wait until therapy is functioning properly again. These factors may increase overall therapy efficacy and patient quality of life.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 8A, 8B and 8C are conceptual diagrams of example patient postures detectable by the sensor within the IMD.

DETAILED DESCRIPTION

Figure 1:
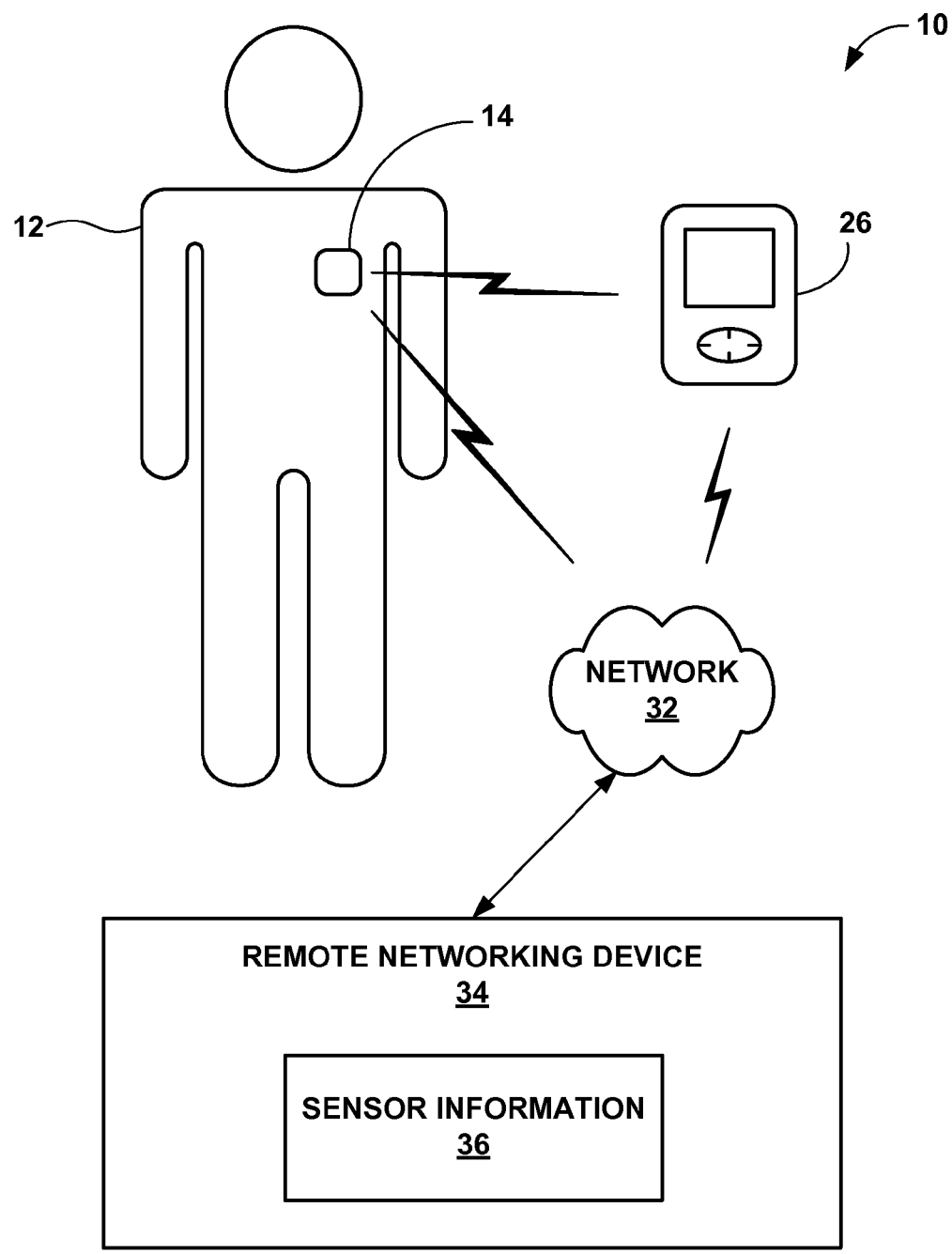
FIG. 1 is a conceptual diagram illustrating an example system that allows sensor information to be transmitted from an implantable medical device (IMD) to a remote networking device for remote calibration of an implantable sensor of the IMD via a network.

As described herein, an implantable sensor may be remotely calibrated by or through the use of a remote networking device. The sensor may be remotely calibrated by a clinician or other user of the remote networking device. In other embodiments, the sensor may be automatically calibrated by the remote networking device.

The implantable sensor generates a signal as a function of at least one of activity, motion, or posture of a patient. The sensor may be part of an implantable medical device (IMD), which may monitor the patient via the sensor and deliver a therapy to a patient. An IMD comprising a sensor according to the present invention does not necessarily deliver therapy.

In embodiments in which the IMD delivers therapy, the IMD may use signals generated by the sensor to adjust or modify therapy in order to optimize therapy efficacy for the current activity, motion, or posture of the patient. For example, the IMD may deliver therapy according to a certain program when the patient is standing, and another program when the patient is lying down. In other embodiments, adjustment of therapy based on activity, motion, or posture may be in a finer gradation than a simple binary choice between two programs. In either case, as a result of such automatic adjustments, the patient may need to less frequently adjust therapy using a manual mode available on an external programmer. However, any problems with the calibration settings of the sensor may affect the ability of the sensor to correctly identify a particular patient activity, motion, or posture. The failure to correctly identify an activity, motion, or posture may result in delivery of ineffective or inappropriate therapy to the patient, e.g., may result in delivery of a therapy associated within a different activity, motion, or posture.

Over time, the sensor may need to be calibrated, e.g., recalibrated, in order to maintain therapy efficacy. In some embodiments, the IMD may identify a potential problem with the current calibration of the sensor. For example, the IMD may identify the potential problem based on a non-physiological change in the sensor output, or unusual readings from another sensor that indicate decreased therapy efficacy resulting from miscalibration of the sensor. In other embodiments, the patient may detect a problem with the sensor, e.g., by detecting that a therapy controlled based on the sensor is unusual or ineffective. In some embodiments, the patient may observe problems with the configuration of the sensor based therapy, for example, observing unusual sensitivity to transitions in activity, motion, posture, or the like. In any case, in response to potential problem, sensor information that is determined based on the signal generated by the sensor is transmitted to the remote networking device via the network. The sensor information may be transmitted by the IMD, or a programming device for the IMD.

A clinician or other user of the remote networking device may be able to review current calibration settings, sensor information, and other data and, if necessary, provide new calibration settings for the sensor, via the network. In other embodiments, the remote networking device may automatically generate new calibration settings for the sensor based on the received sensor data. In either case, the sensor may be calibrated without requiring the clinician to meet the patient face-to-face. The new calibration settings may be remotely generated by remotely interrogating the sensor and/or communicating with the patient in order to associate sensor output with patient postures.

Problems resulting from miscalibration of a sensor are not limited to delivery of inappropriate stimulation. As stated above, the invention is not limited to embodiments in which the sensor is located within an IMD that deliver stimulation, or embodiments in which the sensor output is used to control therapy. In some embodiments, miscalibration of an implantable sensor may lead to misdiagnosis of the patient or misevaluation of the efficacy of a therapy. Whether or not the sensor is included within an IMD or used for control of therapy, the techniques described herein may be used to remotely calibrate the sensor.

FIG. 1 is a conceptual diagram illustrating an example system 10 that allows sensor information 36 to be transmitted from an implantable medical device (IMD) 14 to a remote networking device 34 for remote calibration of a sensor (not shown) within the IMD via a network 32. In addition to IMD 14, system 10 includes an external programmer 26, and a remote networking device 34 that receives sensor information 36 from either external programmer 26 or IMD 14 via a network 32. A clinician may use remote networking device 34 to remotely calibrate the sensor, or remote networking device 34 may automatically calibrate the sensor. IMD 14 and external programmer 26 may be considered local devices in that they may be carried on or within patient 12.

IMD 14 may deliver electrical stimulation therapy, drug therapy, or both to patient 12. Accordingly, IMD 14 may be an implantable pulse generator that delivers electrical stimulation therapy to patient 12 in the form of electrical pulses, an implantable drug pump that delivers a drug or other agent to patient 12 via a catheter, e.g., for alleviation of pain by intrathecal drug delivery, or a device or devices that deliver both neurostimulation therapy and drug therapy to patient 12.

IMD 14 may deliver therapy according to one or more programs. Each program may include values for a number of parameters, and the parameter values define the therapy delivered according to that program. In embodiments where IMD 14 delivers electrical stimulation therapy in the form of electrical pulses, the parameters may include voltage or current pulse amplitudes, pulse widths, pulse rates, electrode combinations, polarities of selected electrodes, and the like. In embodiments where IMD 14 includes a drug pump instead of or in addition to a neurostimulator, program parameters may define flow rates, agent types or concentrations, or infusion types, e.g., continuous or bolus.

The sensor within IMD 14 may be used by the IMD or external programmer 26 to at least partially determine when a given program is used by the IMD to provide therapy to patient 12. The sensor may output a signal as a function of at least one of activity level, motion, or posture of patient 12. The sensor within IMD 14 may also output signals that are indicative of profiles of transitions between states or functions, such as sequences in time of activities, motions, or postures. For example, an upright posture followed in time by a forward lean and then another upright posture might be indicative of the transition from sitting to standing. These changes in posture would, in this example, cause an output signal indicative of the transition profile for standing from a sitting position. In this manner, the sensor may allow IMD 14 or programmer 26 to alter therapy based upon, as examples, the current activity level, motion, or posture of patient 12.

External programmer 26 in FIG. 1 may be an external programmer with which patient 12 interacts to control the delivery of therapy by IMD 14. For example, patient 12 may use external programmer 26 activate or deactivate therapy and select the program that will be used by IMD 14 to delivery therapy at any given time. Patient 12 may also use external programmer 26 to make adjustments to programs, such as amplitude or pulse rate adjustments.

Generally, external programmer 26 or IMD 14 stores programs selected during an initial programming session and any subsequent programming session. A clinician may select the program during a programming session using a clinician programmer and transmit the selected programs to external programmer 26 or IMD 14. Where the programs are stored in external programmer 26, external programmer 26 may transmit programs selected by patient 12 to IMD 14 for delivery of therapy to patient 12 according to the selected program. Where the programs are stored in IMD 14, external programmer 26 may display a list of programs stored within IMD 14 to patient 12, and transmit an indication of the selected program to IMD 14 for delivery of therapy to patient 12 according to the selected program.

In addition, IMD 14 or external programmer 26 may associate programs selected by patient 12 with the current output of the sensor in order to detect the similar output at a later time and adjust therapy accordingly. IMD 14 and external programmer 26 may communicate with each other via local wireless communication. In some embodiments, the external programmer 26 may communicate with IMD 14 and via remote telemetry techniques known in the art, communicating via a local area network (LAN), wide area network (WAN), public switched telephone network (PSTN), or cellular telephone network, for example.

As will be described in detail below, external programmer 26, IMD 14, or both record and utilize sensor information 36 during the operation of the IMD. Remote networking device 34 may receive sensor information 36 from external programmer 26 or another network access point via network 32. The term "sensor information" in this disclosure refers to any raw or processed output of the sensor in addition to calibration settings or other parameters used to operate the sensor. The sensor information may be used to change programs during therapy according to the activity, motion, or posture of patient 12, or to collect data to monitor the activity, motion, or posture of patient 12 for any other purpose. In some embodiments, remote networking device 34 presents sensor information 36 to an authorized user, such as a clinician, technician, or manufacturer, to assist the user in monitoring therapy and/or taking appropriate action. In some examples, sensor information 36 may be presented as charts, diagrams, histograms, and other graphical representations to allow the user to more easily interpret the information.

Based upon the sensor information, the clinician, for example, may be able to interact with IMD 14 in order to modify one or more programs or calibrate the sensor by providing new calibration settings, for example. The clinician may communicate with IMD 14 in real time or on an opportunistic basis. Communication on an opportunistic basis may involve IMD 14 and remote networking device 34 communicating with some intermediate server or other intermediate networking device within network 32 as convenient, e.g., when a network connection is available or a user initiates such communication.

Further, the clinician may provide new calibration settings in the form of an action request. Once IMD 14 receives the action request, IMD 14 may perform the action requested by the clinician in real-time or at some other scheduled or opportunistic time. After IMD 14 performs the action, the IMD 14 may transmit the results or confirmation from the performed action to remote networking device 34 so that the clinician can review the results. For example, the action request may require that IMD 14 recalibrates the sensor by associating sensor output to programs selected by patient 12 over a selected period of time. After the calibration time has elapsed, IMD 14 may transmit the new calibration settings, as sensor information 36, to remote networking device 34 for review by the clinician.

Sensor information 36 may be generated and stored within IMD 14 until the sensor information is transmitted to external programmer 26 and/or remote networking device 34. The processor within IMD 14 may continually or periodically monitor the output of the sensor that may be of interest to the clinician. Certain sensor output thresholds may be used to begin frequent monitoring. In other embodiments, IMD 14 may generate sensor information 36 and immediately transmit the sensor information to external programmer 26 or remote networking device 34 via network 32. In any case, sensor information 36 may be monitored as desired by the clinician.

System 10 may alter the generation and transmission of sensor information 36 during therapy. For example, sensor information 36 may be monitored and transmitted frequently at the beginning of therapy to allow the clinician to review initial patient 12 activity, motion, or posture, or any problems with the therapy. As patient 12 becomes experienced in using system 10 for therapy, sensor information 36 may be monitored and/or stored less frequently. However, sensor information 36 may be monitored or sampled consistently throughout therapy when the output of activity sensor is paramount to therapy efficacy.

In one example, IMD 14 communicates with external programmer 26 and uses the external programmer as an access point to network 32. In another example, IMD 14 communicates wirelessly to a base station or other device that provides an access point for IMD 14 to network 32. In any case, IMD 14 may transmit sensor information 36 to remote networking device 34 via network 32. IMD 14, external programmer 26, remote networking device 34, or any other device of system 10 may implement any number of security protocols to ensure that sensor information 36 and any other data private to patient 12 may not be easily intercepted over network 32. For example, the devices of system 10 may implement private and public key encryption to authenticate data. These and any other security measures known in the art may be implemented to ensure the privacy of patient 12 data.

Network 32 may be any combination of wired or wirelessly connected devices capable of transmitting data between two or more devices. Network 32 may include a local area network (LAN), a wide area network (WAN), a landline telephone network, a cellular phone network, the Internet, a wireless network, or any other communication or data network. Network 32 may be always operating such that sensor information 36 may be transmitted over network 32 at any time determined by IMD 14, external programmer 26, remote networking device 34, patient 12, or the clinician. In this manner, sensor information 36 may be transmitted during a programming session, during and/or immediately after delivery of a program, on demand, according to a schedule, or on an opportunistic basis. When receiving sensor information 36 on demand, patient 12 or the clinician may initiate the transmission of the sensor information from external programmer 26 to remote networking device 34.

Remote networking device 34 may be any type of device that the clinician may use to review sensor information 36, communicate with IMD 14 or external programmer 36, or generate an action request. For example, remote networking device 34 may be a workstation computer, notebook computer, personal digital assistant (PDA), clinician programmer, or any other computing device with access to network 32, and thereby, to IMD 14. Remote access to sensor information 36 may allow the clinician to supervise the efficacy the patient 12 therapy and the operation of IMD 14, whether the clinician is in the clinic, hospital, home, or any other location away from patient 12. The clinician, or any other user of remote networking device 34, may be required to enter a password in order to access the remote networking device. Alternatively, remote networking device 34 may have a biometric input device that receives a biometric from the clinician before access to the remote networking device is approved.

Remote networking device 36 may include multiple devices or components that allow the remote networking device to function as described herein. For example, remote networking device 36 may include a communications circuit (not shown) that receives the sensor information via network 32, receives a signal generated from the sensor, transmits calibration settings to IMD 14 or external programmer 36, and receives a check sensor indication. The communications circuit may handle all of the data received by or sent from remote networking device 36. In addition, remote networking device 36 includes a processor to perform the functions of generating calibration settings and analyzing the senor information and a user interface that allows the user to receive information from and provide input to remote networking device 36.

Sensor information 36 may be routed through one or more servers before reaching remote networking device 34. For example, sensor information 36 may be transmitted from IMD 14 to network 32 before reaching a server that further relays the sensor information. The server may then send the sensor information 36 to remote networking device 36. The server may be operated by the manufacturer of IMD 14 in order to support the operation of IMD 14 and provide services to patient 12 and the clinician. In some examples, an additional server associated with the hospital or clinic of the clinician may receive sensor information 36 from the manufacturer server and deliver the sensor information to remote networking device 34.

The server associated with network 32 may route data to and from IMD 14 or external programmer 26 through a webpage accessible by remote networking device 34. The webpage may be secure and allow an interface for the clinician to access data from IMD 14, such as sensor information 36. The webpage may provide sensor information 36 after the server has analyzed raw data delivered to the server from IMD 14. The webpage may also allow the clinician to send sensor information 36 for analysis by a technician when the clinician believes that IMD 14 or the sensor may be malfunctioning. In essence, the webpage hosted by the server may be the hub of patient 12 therapy. In this manner, remote networking device 34 may be any computing device that simply acts as an access point for the clinician into the therapy of patient 12. Further, the information stored within the server may be made available for analysis by academic or corporate researchers when the data is not private or has been made anonymous. In this manner, such a network architecture may facilitate manufacturer updates or modification to IMD 14 in order to improve therapy. Levels of access to data in the server may be controlled by the server based on user profiles established by an administrator and stored in a memory of the server.

The server may comprise a single computing device or processor, or a plurality of computing devices and/or processors that cooperate to provide the functionality ascribed to the server herein. Data may be stored within a single computing device or memory, or within a plurality of computing devices and/or memories. The server may include a memory that stores program instructions that when executed cause the server to perform the functions ascribed to the server herein. The server memory may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

While system 10 is shown in FIG. 1 as including patient 12, IMD 14, external programmer 26, network 32, and remote networking device 34, system 10 may include additional devices as necessary or desired by the manufacturer or clinician. For example, system 10 may include multiple external programmers 26 and/or multiple remote networking devices 34. In addition, system 10 may utilize one or more servers, databases, data repositories, or other devices capable of transmitting and storing sensor information 36. In this manner, system 10 may, in some examples, be capable of connecting many patients 12 with many clinicians located at any location around the world.

Further, in some embodiments, remote networking device 34 may automatically or semi-automatically perform any of the remote calibration methods described herein. In such embodiments, remote networking device 34 may take the form of a server that analyzes sensor information 36, or generates new calibration settings for sensor. Remote networking device 34 may automatically interact with IMD 14 or patient 12 as described herein with limited or no supervision by a clinician. In such embodiments, remote networking device 34 may determine new calibration settings, but may also present such settings to a clinician or other remote user prior to providing such settings to IMD 14.

Figure 2:
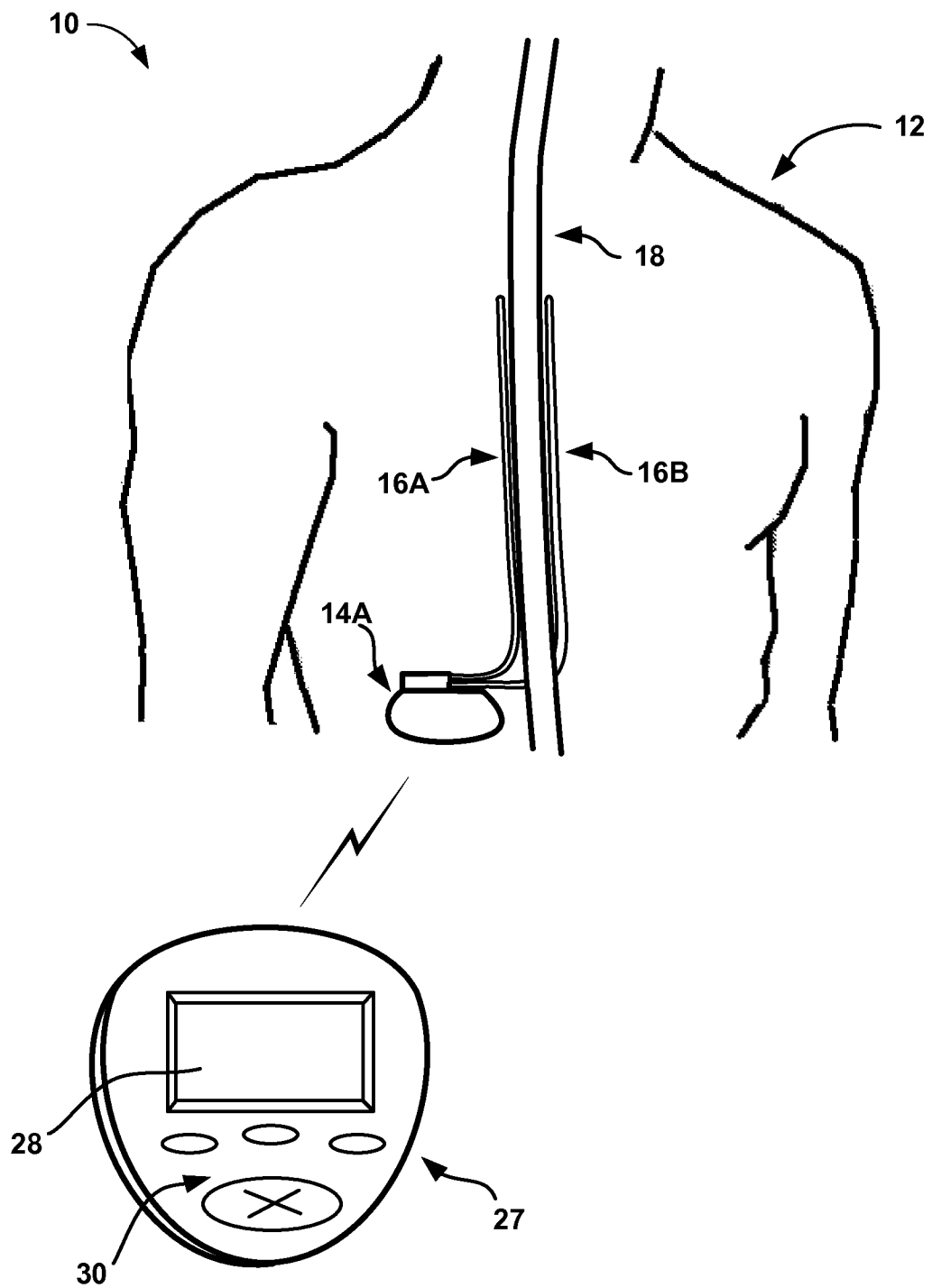
FIG. 2 is a conceptual diagram illustrating an example system for delivering therapy to a patient.

FIG. 2 is a diagram illustrating an example system 10 for delivering therapy to patient 12 via IMD 14. System 10 also includes a patient programmer 27, which is an embodiment of external programmer 26 shown in FIG. 1. As shown in FIG. 2, IMD 14 delivers electrical stimulation therapy or drug delivery therapy to patient 12 via leads 16A and 16B (collectively "leads 16"). Leads 16 may, as shown in FIG. 2, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 2 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence or gastroparesis. In addition, leads 16 may be implanted on or within the heart (not shown) for the provision of cardiac pacing therapy. In other embodiments, leads 16 may be replaced by one or more catheters which deliver a drug to spinal cord 18. In some examples, IMD 14 may even provide a combination electrical stimulation therapy and drug delivery therapy.

As described above, IMD 14 may deliver therapy according to a program comprising values for a plurality of therapy parameters. In embodiments where IMD 14 delivers electrical stimulation therapy in the form of electrical pulses, the parameters may include voltage or current pulse amplitudes, pulse widths, pulse rates, and the like. Further, each of leads 16 includes electrodes (not shown in FIG. 2), and the parameters for a program may include information identifying which electrodes have been selected for delivery of pulses according to the program, and the polarities of the selected electrodes. In some embodiments, IMD 14 may deliver electrical stimulation therapy according to a group of programs.

Each program of a program group may be designed to address a particular symptom of patient 12. For example, in the case of SCS, each program may be designed to reduce the pain experienced by patient 12 in a different location of the body of patient 12. Further, IMD 14 may deliver electrical stimulation therapy according to multiple programs of a group at substantially the same time. For example, in embodiments where IMD 14 delivers electrical stimulation therapy as electrical pulses, each pulse may be delivered according to a different program of the group. Thus, a series of n pulses may deliver therapy according to n different programs. Delivery of electrical stimulation therapy according to program groups may allow IMD 14 to address the symptoms of patient 12 more completely than if single program therapies were delivered. Moreover, substantially simultaneous delivery of the programs of a program group may make the delivery of electrical stimulation therapy more comfortable for patient 12 to the extent that it prevents patient 12 from sensing program changes.

As mentioned previously, IMD 14 includes at least one a sensor which generates a signal as a function activity level, motion, and/or posture of patient 12, which IMD 14 or patient programmer 27 may use to determine which program or group to use in delivering therapy to patient 12. For example, based on the output of the sensor, the IMD or programmer may determine whether patient 12 is sitting, lying down, sleeping, standing, running, walking, experiencing gait, tremor, or other movement disorder symptoms, or the like. Based on the signal generated by the sensor, IMD 14 or programmer 27 may select a program or group for delivery of therapy by the IMD that is appropriate for such situations.

Patient programmer 27, as shown in FIG. 2, is a handheld computing device. Patient programmer 27 may also include a display 28 and a keypad 30, to allow patient 12 to interact with patient programmer 27. In some embodiments, display 26 may be a touch screen display, and patient 12 may interact with patient programmer 27 via display 28. Patient 12 may also interact with patient programmer 27 using peripheral pointing devices, such as a stylus or mouse.

Patient 12 may use patient programmer 27 to control the delivery of electrical stimulation therapy by IMD 14. Patient 12 may use patient programmer 27 to activate or deactivate electrical stimulation therapy and, as will be described in greater detail below, may use patient programmer 27 to select the program or group that will be used by IMD 14 to deliver electrical stimulation therapy from one or more lists of programs or groups. Further, patient 12 may use patient programmer 27 to make adjustments to programs or groups, as will be described in greater detail below. In addition, patient programmer 27 may receive and store sensor information 36 in a memory of the patient programmer. Patient programmer 27 may analyze and/or transmit sensor information 36 to remote networking device 34 via network 32.

Allowing patient 12 greater control over the delivery of electrical stimulation therapy within limits set by the clinician using patient programmer 27 may lead to more effective therapy and efficient use of clinician time. Patient 12 may be able to select programs or program groups, and make adjustments in order to address changes in symptoms, which may occur throughout the day, or based on changes in the position, posture, or activity level of the patient. In this manner, patient 12 may manually associate the output of the activity sensor with activities performed by the patient. These modifications and improvements to electrical stimulation therapy may occur without clinician intervention, or in addition to remote access by a clinician via remote networking device 34. Further, the clinician may be able to spend less time initially programming electrical stimulation therapy for patient 12 by providing a variety of programs or program groups at implant from which patient 12 may choose, allowing patient 12 to experiment with the programs or groups, and optimize, improve, or tailor the electrical stimulation therapy over time.

System 10 may also include a clinician programmer (not shown) similar to patient programmer 27 and having additional features. The clinician programmer may be a handheld computing device that includes a display, such as a LCD or LED display, to display information to a user. The clinician programmer may also include a keypad which may be used by a user to interact with the clinician programmer. In some embodiments, the display may be a touch screen display, and a user may interact with the clinician programmer via the display. A user may also interact with the clinician programmer using peripheral pointing devices, such as a stylus or mouse. The keypad may take the form of an alphanumeric keypad or a reduced set of keys associated with particular functions. In some embodiments, remote networking device 34 may function similar to the clinician programmer.

A clinician (not shown) may use the clinician programmer to program electrical stimulation therapy for patient 12. As will be described in greater detail below, the clinician may select existing programs or specify programs by selecting program parameter values, and test the selected or specified programs on patient 12. The clinician may receive feedback from patient 12, and store information identifying the programs and rating information associated with the programs as a session log for patient 12. The clinician may use the session log to more quickly select effective programs, which may be included in groups, for delivery of electrical stimulation therapy for patient 12. In addition, the clinician may initially calibrate the sensor to patient 12 activity levels, motions, or postures during the programming session.

In addition to programming the therapy parameters for patient 12, the clinician may also configure parameters that affect the behavior of the sensing system. These parameters may be system parameters that could include increasing or decreasing sensor sensitivity, adding a length of hysteresis or degree of hysteresis to the sensor calibration to avoid unwanted transitions, and determining the rate of change in therapy parameters between one activity, motion, or posture and another. In this manner, the clinician may have the ability to adjust and configure the overall therapy delivered to patient 12. In alternative embodiments, patient programmer 27 may allow patient 12 to adjust some of these system parameters within a range predetermined by the clinician.

Programs or program groups programmed by the clinician using the clinician programmer may be transmitted to and stored within one or both of patient programmer 27 and IMD 14. Where the programs or groups are stored in patient programmer 27, patient programmer 27 may transmit the program or group selected by patient 12 to IMD 14 for delivery of electrical stimulation therapy to patient 12 according to the selected program or group. Where the programs or groups are stored in IMD 14, patient programmer 27 may receive a list of programs or groups from IMD 14 to display to patient 12, and transmit an indication of the selected program or group to IMD 14 for delivery of electrical stimulation therapy to patient 12 according to the selected program or group. Either IMD 14 or patient programmer 27 may select a program or program group based on the signal generated by the sensor, and collect sensor information for transmittal to remote networking device 34.

Figure 3:
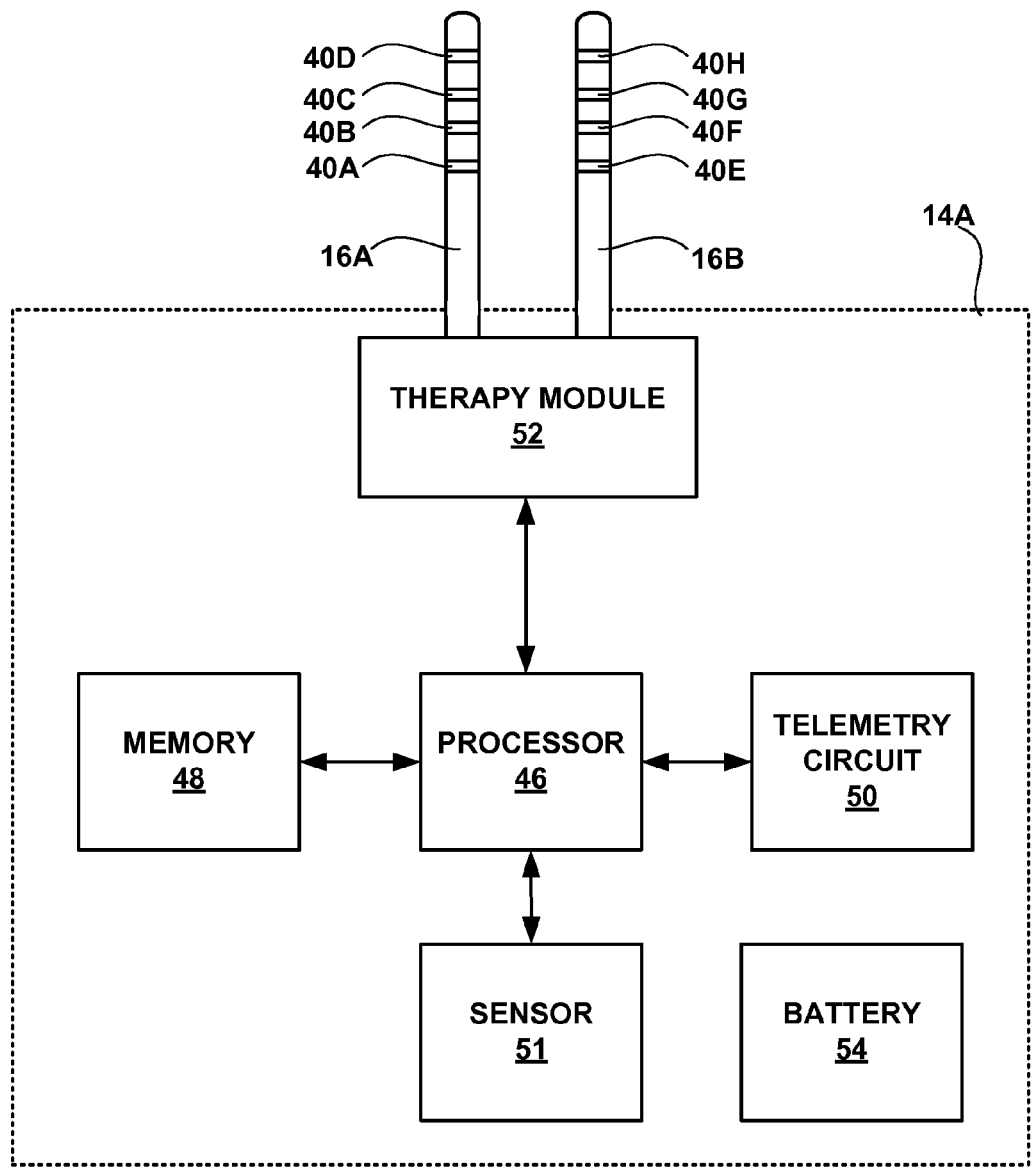
FIGS. 3 and 4 are block diagrams illustrating example implantable medical devices for delivering electrical stimulation therapy and drug delivering therapy, respectively, to the patient.

FIG. 3 is a block diagram illustrating an IMD 14A, which is an example of an IMD 14 that delivers electrical stimulation therapy to patient 12 according to one or more programs or program groups. IMD 14A may deliver electrical stimulation therapy via electrodes 40A-H of lead 16A and electrodes 40I-P of lead 16B (collectively "electrodes 40"). Electrodes 40 may be ring electrodes or segmented electrodes. The configuration, type and number of electrodes 40 illustrated in FIG. 3 are merely exemplary.

Electrodes 40 are electrically coupled to a therapy module 52 via leads 16. Therapy module 52 may, for example, include an output pulse generator coupled to a power source such as a battery. Alternatively, therapy module 52 may produce continuous electrical signals, e.g. a sine wave. Therapy module 52 may deliver electrical pulses to patient 12 via at least some of electrodes 40 under the control of a processor 46.

Processor 46 may control therapy module 52 to deliver electrical stimulation therapy according to a selected program or program group. Specifically, processor 46 may control therapy module 52 to deliver electrical pulses with the amplitudes and widths, and at the rates specified by the selected program, or the programs of the selected program group. Processor 46 may also control therapy module 52 to deliver the pulses via a selected subset of electrodes 40 with selected polarities, as specified by the one or more programs. Processor 46 may control therapy module 52 to deliver each pulse according to a different program of a program group. In addition, processor 46 may monitor the output from a sensor 51 and select a program or program group for therapy based upon the output of the sensor. Processor 46 may include a microprocessor, a controller, a DSP, an ASIC, an FPGA, discrete logic circuitry, or the like.

IMD 14A also includes a memory 48. In some embodiments, memory 48 may store programs or program groups that are available to be selected by patient 12 for delivery of electrical stimulation therapy. In some embodiments, processor 46 may generate sensor information 36 based on the signals output by sensor 51, and store sensor information 36 in memory 48. Processor 46 may generate sensor information 36 by monitoring the output of sensor 51 over the course of therapy. In some examples, processor 46 associates the output of sensor 51 with specific programs or groups stored in memory 48. In this manner, processor 46 may generate a lookup table or similar algorithm for selecting the appropriate program or group for therapy based upon the detected activity level, motion, or posture of patient 12. Memory 48 may also include program instructions that, when executed by processor 46, cause IMD 14A to perform the functions ascribed to IMD 14A herein. Memory 48 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Sensor 51 may be any type of sensor that is capable of detecting the activity level, motion, or posture of patient 12. In some examples, IMD 14 may include multiple sensors 51 within IMD 14 and located throughout patient 12. Sensor 51 may preferably be a multi-axis accelerometer in order to detect movement or orientation of patient 12 in any direction in space. Other types of sensors 51 may include a bonded piezoelectric crystal, a mercury switch, or a gyro, magnetometers, or any other sensor used in the art. Example patient states that sensor 51 is capable of detecting may include postures such as standing, reclining, sitting, or laying horizontally. In addition, sensor 51 may detect walking, running, bicycling, jumping, swimming, or any other physical activity engaged by patient 12. Sensor 51 may also detect symptomatic movements or postures, such as those associated with epilepsy or movement disorders. Patient 12 may utilize external programmer 26 to aid IMD 14 in recognizing which outputs from sensor 51 correspond to which activity engaged by patient 12. External programmer 26 may have a diary like interface for performing this association or may prompt the patient for input after certain events or at specified times.

In the embodiment in which sensor 51 is a multi-axis accelerometer, the sensor is affected by the Earth's gravity. Initial calibration of sensor 51 is effective so long as the orientation of IMD 14 within patient 12, e.g., the orientation relative to the patient, remains constant. Depending upon patient 12 anatomy or patient 12 activity, IMD 14 orientation within patient 12 may change due to IMD 14 rotation or inversion, e.g. being flipped. When IMD 14 is not easily returned to its original orientation, the clinician may use remote networking device 34 to communicate with IMD 14, or remote networking device 34 may automatically communicate with IMD 14, in order to recalibrate, e.g., provide new calibration settings for, sensor 51. In some cases, the clinician may simply invert the current calibration settings to correct the output of sensor 51 without fully calibrating the activity sensor. Similarly, other sensed activities or motions may change over time. For example, the posture of patient 12, or speed of transition between postures, may improve as the efficacy of the therapy decreases the severity of adverse symptoms in patient 12. Alternately, such measures of posture may worsen over time as a disease state progresses. All of these changes may be amenable to recalibration of activities, motions, and postures performed via remote networking device 34.

IMD 14A also includes a telemetry circuit 50 that allows processor 46 to communicate with external programmer 26 (FIG. 1.) or another device that connects to network 32. Processor 46 may receive programs to test on patient 12 from the clinician programmer via telemetry circuit 52 during programming by a clinician. Where IMD 14A stores programs or program groups in memory 48, processor 46 may receive such programs or groups from the clinician programmer via telemetry circuit 52 during programming by a clinician, and later receive program or group selections made by patient 12 from external programmer 26 via telemetry circuit 52. Where external programmer 26 stores the programs or groups, processor 46 may receive programs or groups selected by patient 12 from patient programmer 26 via telemetry circuit 52.

Battery 54 is a power source that delivers operating power to the components of IMD 14A. Battery 54 may be a rechargeable battery that is associated with a power generation circuit to produce the operating power. Recharging may be accomplished through proximal inductive interaction between an external charger and an inductive charging coil within IMD 14A. In some embodiments, power requirements may be small enough to allow IMD 14A to utilize patient motion and implement a kinetic energy-scavenging device to trickle charge battery 54. In other embodiments, non-rechargeable traditional batteries may be used for a limited period of time.

Figure 4:
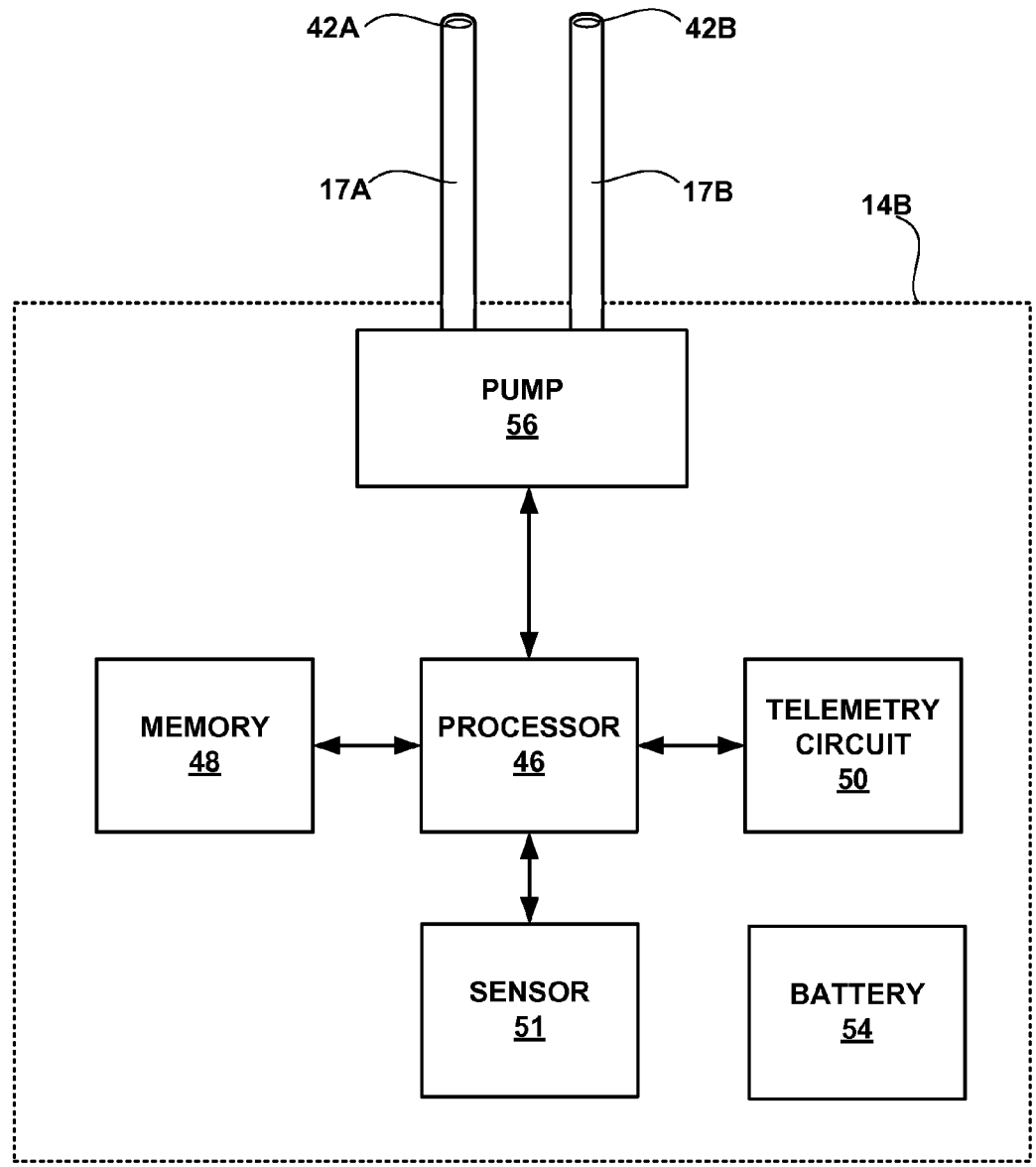

FIG. 4 is a block diagram illustrating an IMD 14B, which is an example of an IMD 14 that delivers drug therapy to patient 12 according to one or more programs. IMD 14B is substantially similar to IMD 14A of FIG. 3, but IMD 14B delivers drugs to patient 12 via pump 56. Pump 56 delivers a drug to patient 12 from a reservoir in IMD 14B (not shown), through catheters 17A and 17B (collectively "catheters 17"), and out of ports 42A and 42B (collectively "ports 42"). The configuration, type and number of catheters 17 and ports 42 illustrated in FIG. 4 are merely exemplary.

Processor 46 controls pump 56 to deliver the appropriate quantity of drug at the desired frequency defined by the therapy parameters. Processor 46 may follow multiple programs throughout the daily routine of patient 12 in order to conserve drug while providing effective therapy. Processor 46 may include a microprocessor, a controller, a DSP, an ASIC, an FPGA, discrete logic circuitry, or the like. Memory 48 contains one or more programs, other data related to the operation of IMD 14B, and any sensed data. In addition, memory 48 may store sensor information 36 generated by processor 46. Memory 48 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like. Sensor 51 operates similarly, and may be used for substantially similar purposes, e.g., selection of programs, in both IMD 14B and IMD 14A (FIG. 3).

Figure 5:
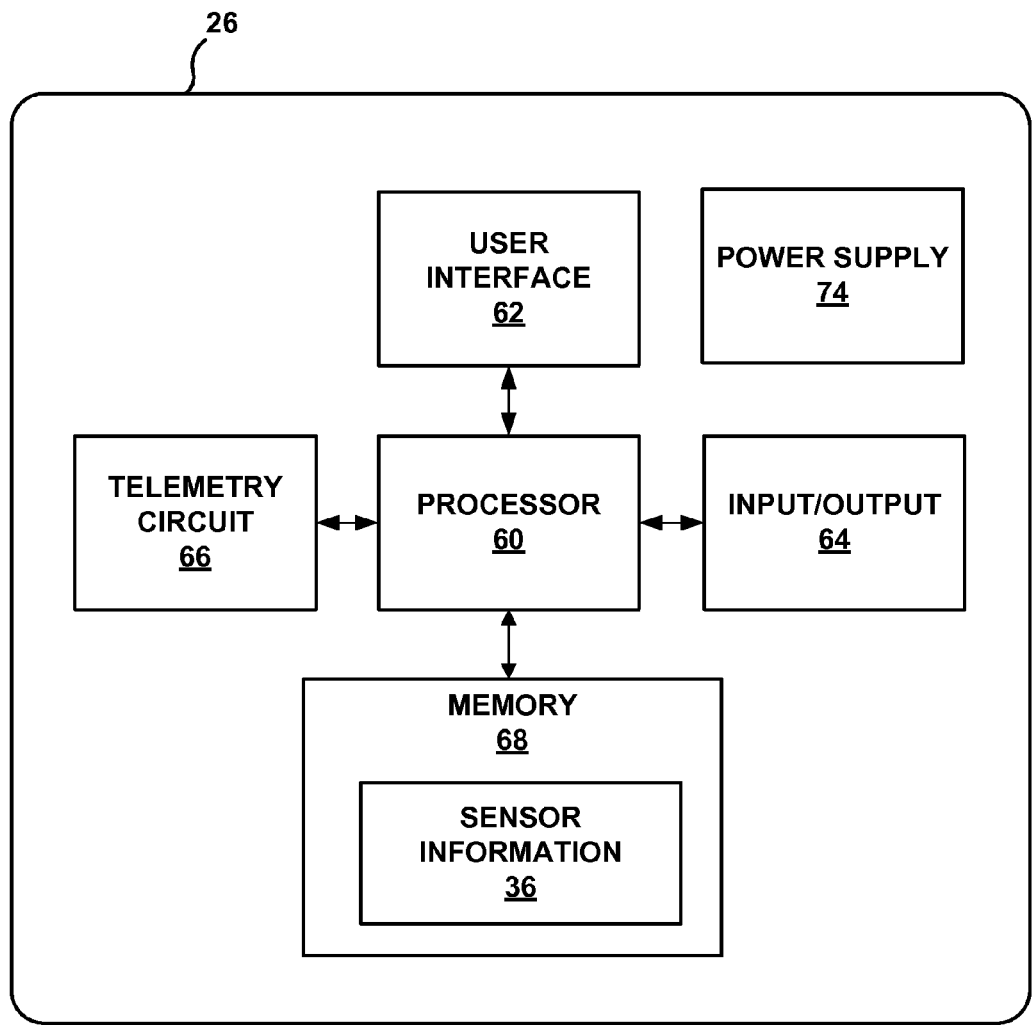
FIG. 5 is a block diagram illustrating an example external programmer that allows control of therapy delivery by the implantable medical device and collects sensor information.

FIG. 5 is a block diagram illustrating an example external programmer 26 that allows control of therapy delivery by an IMD 14 and collects sensor information 36. External programmer 26 may be used to program and adjust therapy. External programmer 26 includes processor 60, user interface 62, input/output 64, telemetry 66, memory 68, and power supply 74. A user may interact with a processor 60 via a user interface 62 to program therapy for patient 12 as described herein. User interface 62 may include a display, keypad, touch screen, peripheral pointing devices, or any other input devices commonly used with computing devices. Processor 60 may also provide a graphical user interface (GUI) via the display to facilitate interaction with a clinician or patient 12. Processor 60 may include a microprocessor, a controller, a DSP, an ASIC, an FPGA, discrete logic circuitry, or the like.

User interface 62 may include functions in addition to programming therapy parameters. For example, the clinician or patient 12 may provide an activity input to user interface 62 that corresponds the current activity, motion or posture sensed by sensor 51. In this manner, sensed postures may be directly correlated to the actual posture that patient 12 is holding. User interface 62 may have dedicated activity buttons, such as buttons for standing, sitting, lying down, etc., or soft buttons programmable by the user. User interface 62 may also accept an activity input at any time or only during a learning mode when enabled. In addition, remote networking device 34 may receive the activity input that corresponds to the current activity, motion or posture of patient 12.

External programmer 26 also includes a memory 68. Memory 68 may include programs or program groups for controlling delivery of therapy by IMD 14. In addition, memory 68 may include sensor information 36. Sensor information 36 stored in memory 68 may be raw data directly from IMD 14, or analyzed information processed by processor 60. Sensor information 36 may be stored in memory 68 from IMD 14 until external programmer 26 can transmit the information to remote networking device 34. Alternatively, memory 68 may store sensor information 36 for the duration of therapy. Memory 68 may also include instructions that, when executed by processor 60, cause external programmer 26 to perform the functions ascribed to external programmer 26 herein. Memory 68 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

A clinician may program electrical stimulation therapy for patient 12 by specifying programs for testing on patient 12 during an electrical stimulation therapy programming session. In some embodiments, the clinician may specify one or more programs for testing by selecting programs suggested as a result of a query to a server, as will be described in greater detail below.

Processor 60 may store the specified programs within memory 68, and transmits specified programs to the server via input/output (I/O) circuitry 64. I/O circuitry may include any known circuitry for wireless or wired access to network 32. The server directs processor 60 to test specified programs by, for example, providing processor 60 with an order for testing of the specified programs. To test a specified program, processor 60 delivers the program to IMD 14 via a telemetry circuit 66 for delivery of therapy according to that program to patient 12.

Telemetry circuit 66 may allow for communications between external programmer 26 and IMD 14 and/or other devices via network 32. In this manner, external programmer 26 may receive sensor information 36 from IMD 14 and transmit the sensor information 36 to other devices, such as remote networking device 36 via network 32. In addition to sensor information 36, external programmer 26 may utilize telemetry circuit 66 to transmit any data to other devices when needed. When data is transmitted from IMD 14 through telemetry circuit 66, processor 60 may only receive data from IMD 14 generated after the last transmission from the IMD. Alternatively, processor 60 may compare data stored in memory 68 with the data from IMD 14 and only store data not already within the memory of external programmer 26.

Power supply 74 may be a battery that is rechargeable or non-rechargeable. The user may recharge the battery of power supply 74 via an AC outlet, inductive coupling, computer Universal Serial Bus (USB), or any other technique known in the art. Alternatively, power supply 74 may draw power from an AC or DC electrical power source when batteries are not necessary.

Figure 6:
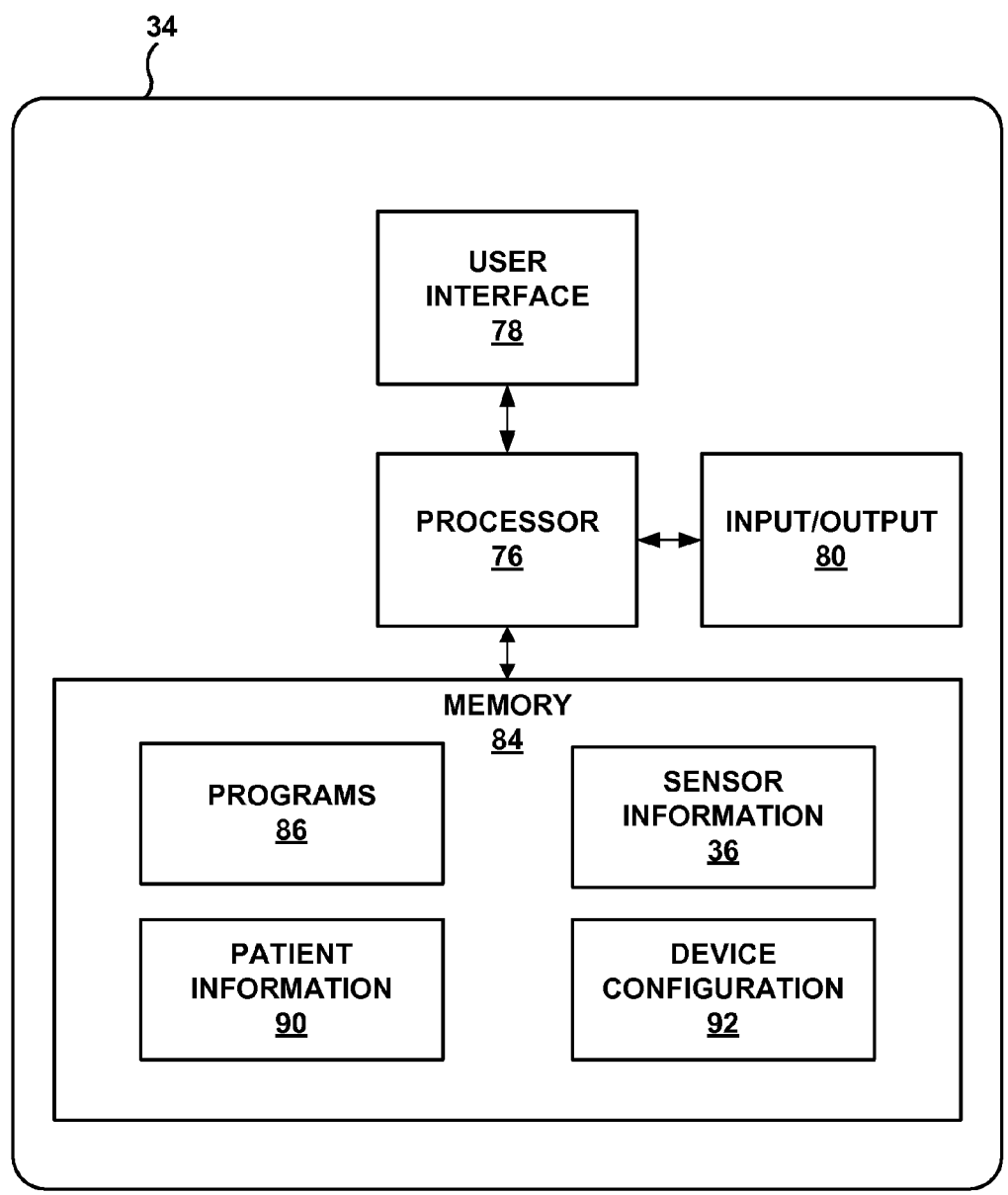
FIG. 6 is a block diagram illustrating an example remote networking device that receives sensor information via a network and interacts with the IMD and/or external programmer to calibrate the sensor when necessary.

FIG. 6 is a block diagram illustrating an example remote networking device 34 that receives sensor information 36 via a network 32 and interacts with IMD 14 and/or external programmer 26 to calibrate the sensor when necessary. Remote networking device 34 may be used by a clinician or field technician to communicate with IMD 14 and/or external programmer 26 remotely. Remote networking device 34 may be used to program and adjust stimulation therapy. In addition, remote networking device 34 may be used to receive sensor information 36 and communicate with IMD 14 in real time and/or transmit action requests in response to the sensor information. Remote networking device 34 includes processor 76, user interface 78, input/output (I/O) circuitry 80, and memory 84. A user may interact with a processor 76 via a user interface 78 to program stimulation therapy for patient 12, review sensor information 36, and communicate with IMD 14, as described herein. User interface 78 may include a display, keypad, touch screen, peripheral pointing devices, or any other input devices commonly used with computing devices such as desktop workstations or notebook computers. Processor 76 may also provide a graphical user interface (GUI) via the display to facilitate interaction with a clinician. Processor 76 may include a microprocessor, a controller, a DSP, an ASIC, an FPGA, discrete logic circuitry, or the like.

Remote networking device 34 also includes a memory 84. Memory 84 may include multiple data sets necessary for patient therapy. As shown, memory 84 may include programs 86, sensor information 36, patient information 90 and device configuration information 92. Programs 86 may include individual programs and groups of programs that each include instructions that IMD 14 may use to deliver therapy to patient 12. Programs 86 may include programs currently used by IMD 14, generated but not transmitted to IMD 14, or used previously by IMD 14. Patient information 90 may include patient condition data, patient history, sensed physiological data, or any other data specifically related to patient 12. Device configuration information 92 may include data identifying the configuration of IMD 14 and/or external programmer 26 in addition to instructions related to method for communication with IMD 14 and/or external programmer 26.

As mentioned previously, sensor information 36 stored in memory 84 may be raw data directly from IMD 14 or analyzed information processed by processor 76. Memory 84 may store sensor information 36 for the duration of therapy or until the clinician reviews the information. Memory 84 may also include instructions that, when executed by processor 76, cause processor 76 to perform any of the functions ascribed to remote networking device 34 herein. Memory 84 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

A clinician may program therapy for patient 12 by specifying programs for testing on patient 12 during a therapy programming session. In some embodiments, the clinician may specify one or more programs for testing by selecting programs suggested as a result of a query to a server or processor 76. The clinician may interact with the user interface 78 in order to specify programs to send to IMD 14 for therapy. Processor 76 may store the specified programs 86 within memory 84 and transmit specified programs 86 to IMD 14 or external programmer 26 via input/output (I/O) 80, which may be any circuitry for wired or wireless access to network 32.

I/O 80 may allow for communications between remote networking device 34 and an access point to network 32 or another device. In this manner, remote networking device 34 may receive sensor information 36 from IMD 14 and/or external programmer 26. In addition to sensor information 36, remote networking device 34 may utilize I/O 80 to transmit any data to other devices when needed. When data is transmitted from remote networking device 34 through I/O, processor 76 may only send data not previously transmitted to the intended device. Alternatively, processor 76 may compare data stored in memory 84 with the data from remote networking device 34 and only store data not already within the memory of remote networking device 34.

In some examples, remote networking device 34 may include one or more security features that only allow authorized users to access the remote networking device. For example, a user, e.g., the clinician, may be required to enter a username and password into user interface 78 that is unique to the user. Remote networking device 34 may also require other information from the user for authentication. Alternatively, remote networking device 34 may require the user to input a biometric that identifies the user for authentication. The biometric may be entered into a personal identifier device that the user carries and communicates with remote networking device 34 to authorize the user to use the remote networking device. The biometric may also be provided to a biometric scanner built into remote networking device 34. Types of biometrics used by remote networking device 34 may include a fingerprint, heart rate, electrocardiogram, retinal scan, face scan, or any other anatomical or physiological characteristic that may be used to identify the user.

Figure 7A:
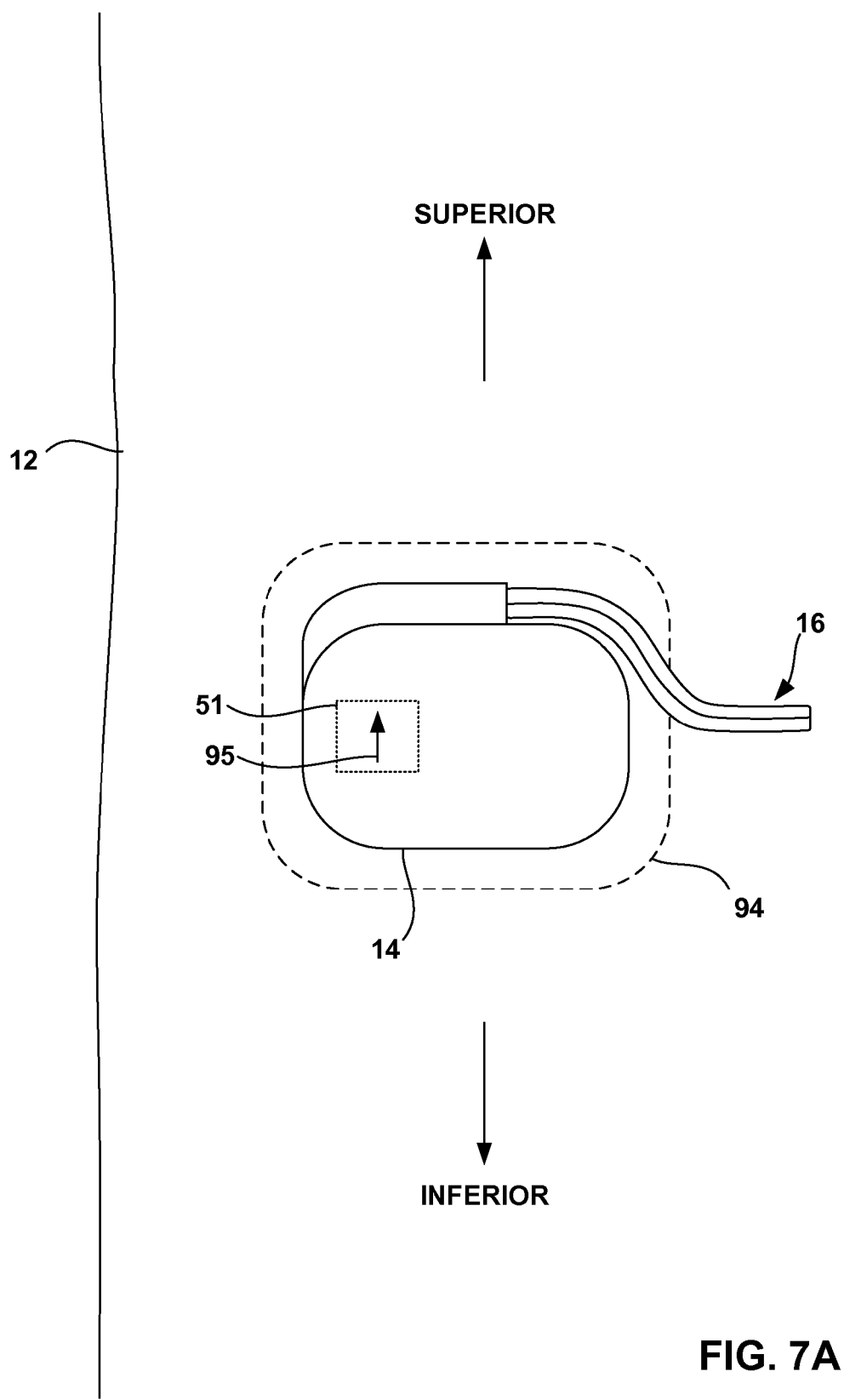
FIGS. 7A and 7B are conceptual diagrams of example orientations of an IMD implanted within a patient.
Figure 7B:
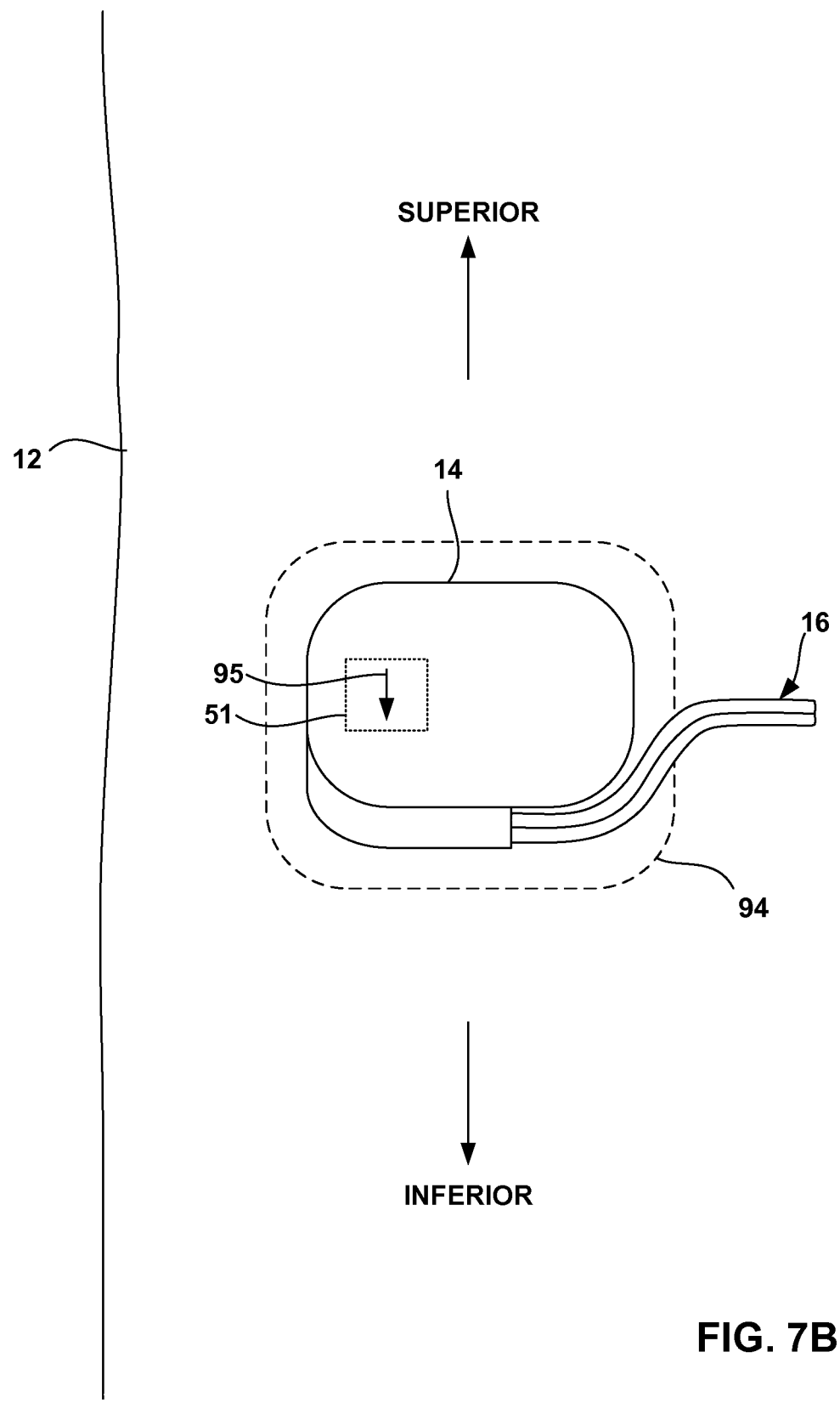

FIGS. 7A and 7B are conceptual diagrams of example orientations of IMD 14 implanted within patient 12. As shown in FIG. 7A, IMD 14 is implanted within patient 12. Specifically, IMD 14 is located within pocket 94 created within the tissue of patient 12. Pocket 94 is generally sized to be just large enough for IMD 14 to fit within pocket 94 without any excess room for the IMD to move. Leads 16 are connected to IMD 14 and leave pocket 94 en route to the stimulation site within patient 12. IMD 14 may be originally implanted such that the side of IMD to which leads 16 connect is in a superior orientation relative to patient 12. Sensor 51 may be initially calibrated based on this orientation, indicated by arrow 95 pointing towards the superior direction of patient 12. Initial calibration of sensor 51 in this case may refer to the association of certain outputs of sensor 51 with activity levels, activities, motions, postures, therapy programs, or therapy program groups when IMD 14 was in the initial orientation.

As shown in FIG. 7B, IMD 14 has flipped within pocket 94 of patient 12. While IMD 14 may still be functional in delivering therapy, sensor 51 is not calibrated correctly with respect to gravity. Therefore, the current orientation of arrow 95 indicates that the activity sensor 51 would determine the superior direction of patient 12 is actually the inferior direction of the patient. In this manner, sensor 51 is inverted and IMD 14 may incorrectly select programs for patient 12 because the sensor is no longer correctly identifying patient 12 activity levels, activities, motions, or postures.

When IMD 14 becomes flipped, inverted, or in any other way moves within pocket 94, therapy efficacy may be affected. In some cases, patient 12 may recognize that program selection no longer matches activity states. Patient 12 may use external programmer 26 to create a check sensor indication that is received by remote networking device 34. In other cases, IMD 14 may recognize that sensor 51 has flipped based upon usual sensor 51 output, or an algorithm that detects patient 12 is upside down or in some other unusual position or posture for a long period of time. IMD 14 may identify that it is misoriented in this situation. IMD 14 may also identify that sensor 51 is misoriented based on an output of another sensor that indicates that therapy efficacy has deteriorated. IMD 14 may transmit a check activity sensor indication to remote networking device 34 in order to allow the clinician to resolve the problem.

Once remote networking device 34 receives the check activity sensor indication, the clinician or remote networking device 34 may take action to correct the calibration setting of sensor 51. The clinician or remote networking device 34 may communicate with IMD 14 and/or patient 12 via external programmer 26 in real time in order to generate new calibration settings based upon the orientation of IMD 14 within pocket 94. Alternatively, the clinician or remote networking device 34 may send an action request to IMD 14 to relearn, or recalibrate, sensor 51 through a preprogrammed algorithm or with the aid of patient 12 with external programmer 26. In addition, the clinician, remote networking device 34, programming device 26, or IMD 14 may associate programs for therapy with the new calibrated output of sensor 51. Recalibration of sensor 51 may occur for any movement of IMD 14 within pocket 94, not only an inverted IMD 14.

FIGS. 8A, 8B and 8C are conceptual diagrams of example patient 12 activities, postures, or orientations detectable by the sensor within IMD 14. As shown in FIG. 8A, sensor 51 of IMD 14 recognizes that patient 12 is standing on ground 96. Sensor 51 may distinguish between standing and walking or running by the orientation of IMD 14 and the frequency of accelerations with respect to ground 96.

FIG. 8B illustrates an example posture of patient 12 lying down on bed 98. The sensor within IMD 14 may detect the horizontal orientation of patient 12 and IMD 14 may change therapy accordingly. FIG. 8C illustrates another posture detectable by the sensor within IMD 14. The sensor of IMD 14 may detect the reclined sitting position of patient 12 in chair 100. IMD 14 may utilize the output of the sensor to adjust therapy according to the patient activity, motion, or posture. Additional activities, motions, or postures may also be detected by IMD 14, as these are merely example postures detectable by the activity sensor.

Aspects related to the time of transitions or the sequence of detected activities, motions, or postures may also be used by the sensor to generate output. For example, a standing (FIG. 8A) to sitting posture (FIG. 8C) change may be associated with a predictable series of intermediate postures which occur in a specified order and with specified timings. Sensor 51 may detect these intermediate changes to appropriately modify the therapy. In addition, system 10 may report changes in intermediate postures that may be associated with improving or worsening patient 12 condition.

Figure 9:
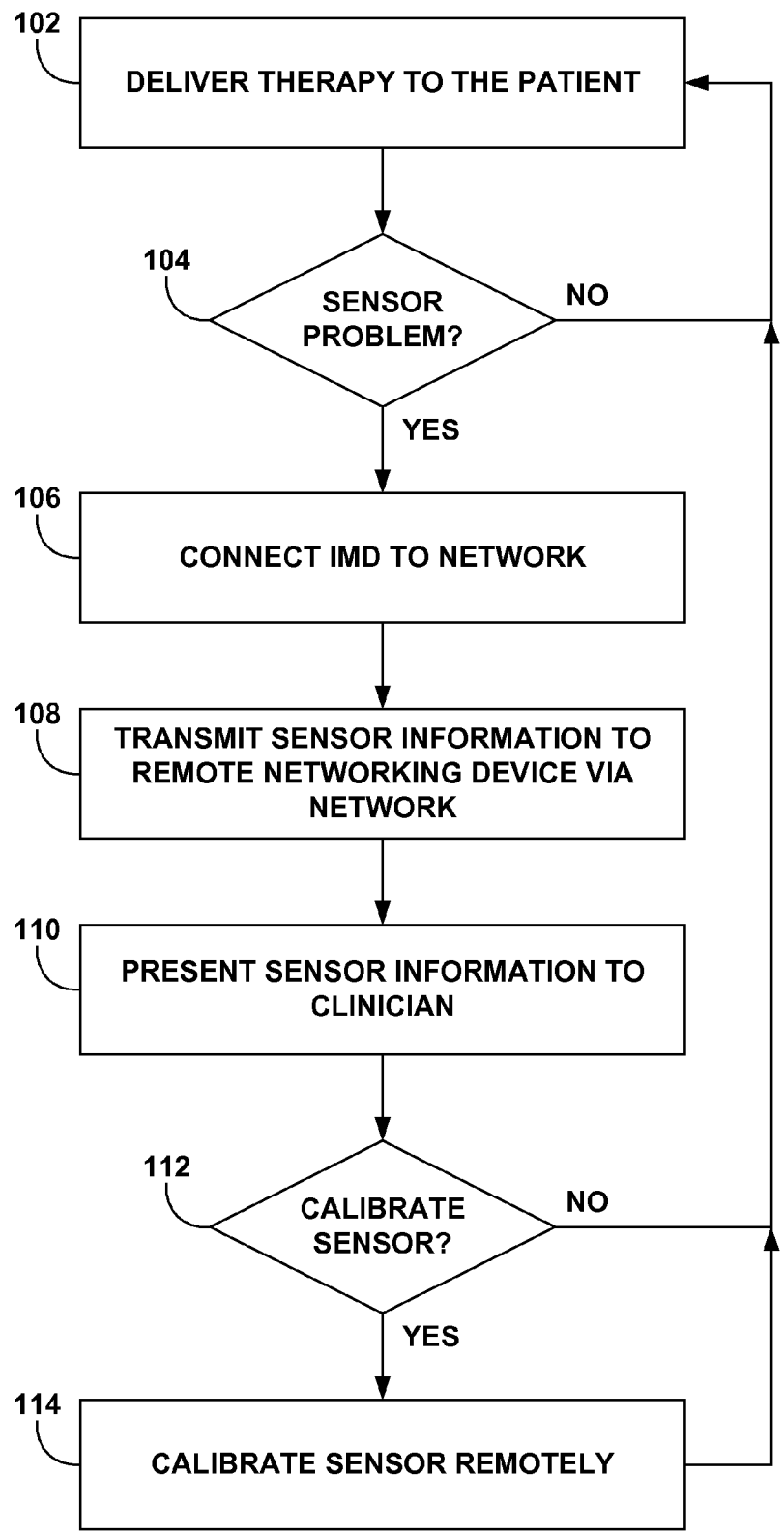
FIG. 9 is a flow diagram illustrating an example technique for transmitting sensor information from an IMD to a remote networking device when the IMD detects a problem with the sensor.

FIG. 9 is a flow diagram illustrating an example technique for transmitting sensor information 36 from IMD 14 to remote networking device 34 when the IMD detects a problem with the sensor output. As shown in FIG. 9, IMD 14 delivers therapy to patient 12 according to one or more programs (102). If processor 46 does not detect any unusual output of sensor 51 (104), IMD 14 continues to deliver therapy as prescribed (102). If processor 46 detects that there is a problem or abnormality with the output of sensor 51 (104), processor 46 initiates connection of IMD 14 to network 32 (106). IMD 14 then transmits sensor information 36 to remote networking device 34 via network 32 (108). In some examples, sensor information 36 may first be transmitted to a server associated with network 32. The server may then transmit sensor information 36 to remote networking device 34.

Once sensor information 36 is received by remote networking device 34, the remote networking device 34 may present sensor information 36 to the clinician (110). As mentioned previously, sensor information 36 may be analyzed and/or presented in any type of graphical or numerical representation desired by the clinician. Based on sensor information 36, the clinician may determine whether or not sensor 51 needs to be recalibrated (112). If sensor 51 does not need calibration, the clinician may instruct IMD 14 to continue delivering therapy (102). If sensor 51 needs calibration, the clinician may calibrate activity sensor 51 remotely by determining new calibration settings for the activity sensor (114). Details regarding remote calibration of activity sensor 51 are provided in FIG. 11.

Figure 10:
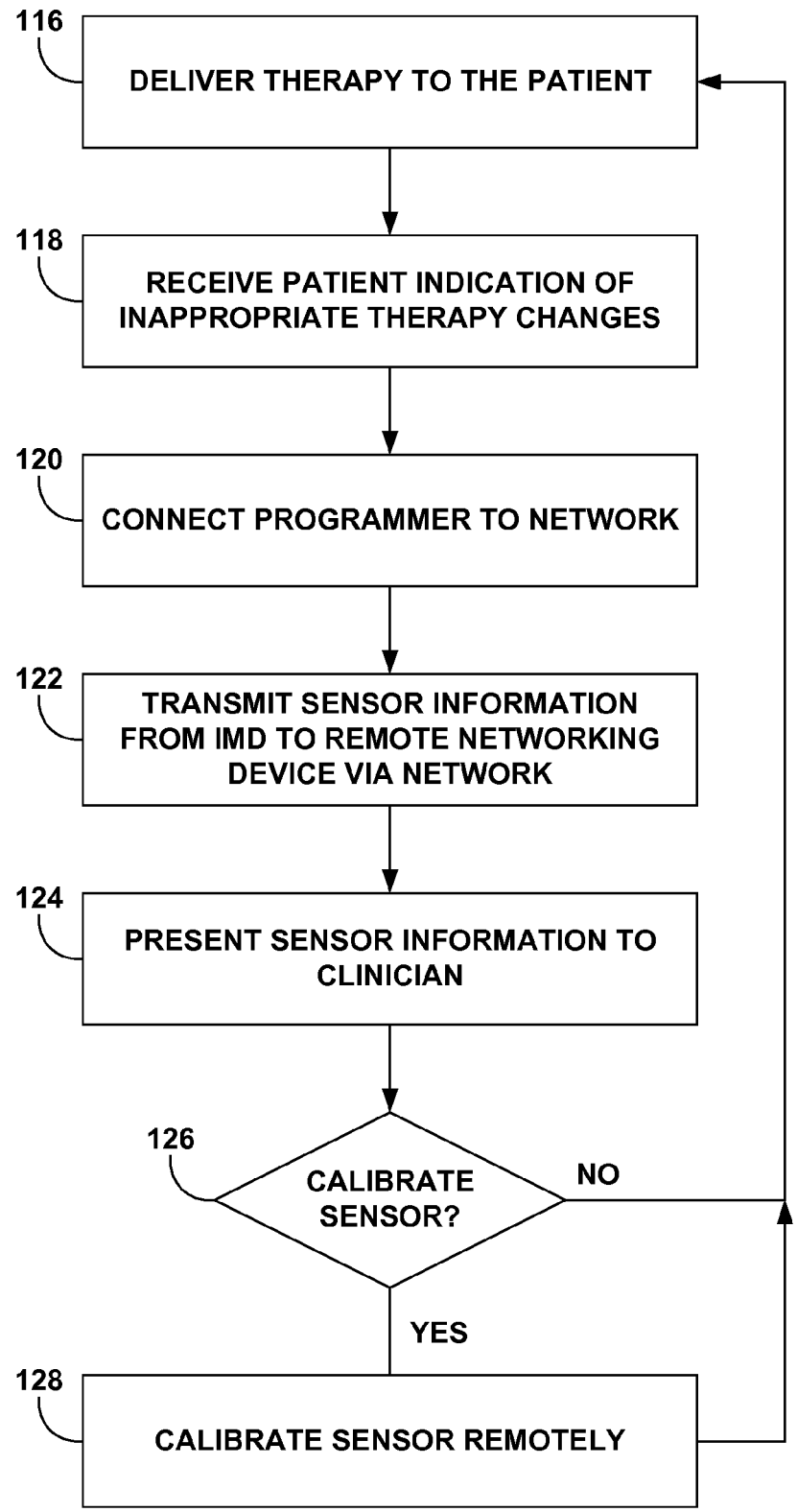
FIG. 10 is a flow diagram illustrating an example technique for transmitting sensor information from an IMD to a remote networking device when the patient detects a problem with therapy changes for different activities.

FIG. 10 is a flow diagram illustrating an example technique for transmitting sensor information 36 from IMD 14 to remote networking device 34 when patient 12 detects a problem with therapy. As shown in FIG. 10, IMD 14 delivers therapy to patient 12 according to one or more programs (116). External programmer 26 receives a patient indication that therapy changes associated with activity, motion, or posture changes are different than expected (118). The patient may provide this indication whenever a problem with therapy is identified as possibly being a problem with sensor 51 calibration. Processor 60 of external programmer 26 then initiates connection of external programmer 26 to network 32 (120). External programmer 26 then transmits sensor information 36 to remote networking device 34 via network 32 (122). In some examples, sensor information 36 may first be transmitted to a server associated with network 32. The server may then transmit sensor information 36 to remote networking device 36.

Once sensor information 36 is received by remote networking device 34, the remote networking device 34 presents sensor information 36 to the clinician (124). As mentioned previously, sensor information 36 may be analyzed and/or presented in any type of graphical or numerical representation desired by the clinician. Based on sensor information 36, the clinician may determine whether or not sensor 51 needs to be recalibrated (126). If sensor 51 does not need calibration, the clinician may instruct IMD 14 to continue delivering therapy (116). If sensor 51 needs calibration, the clinician may calibrate sensor 51 remotely by determining new calibration settings for the sensor (128). Details regarding remote calibration of activity sensor 51 are provided in FIG. 11.

Figure 11:
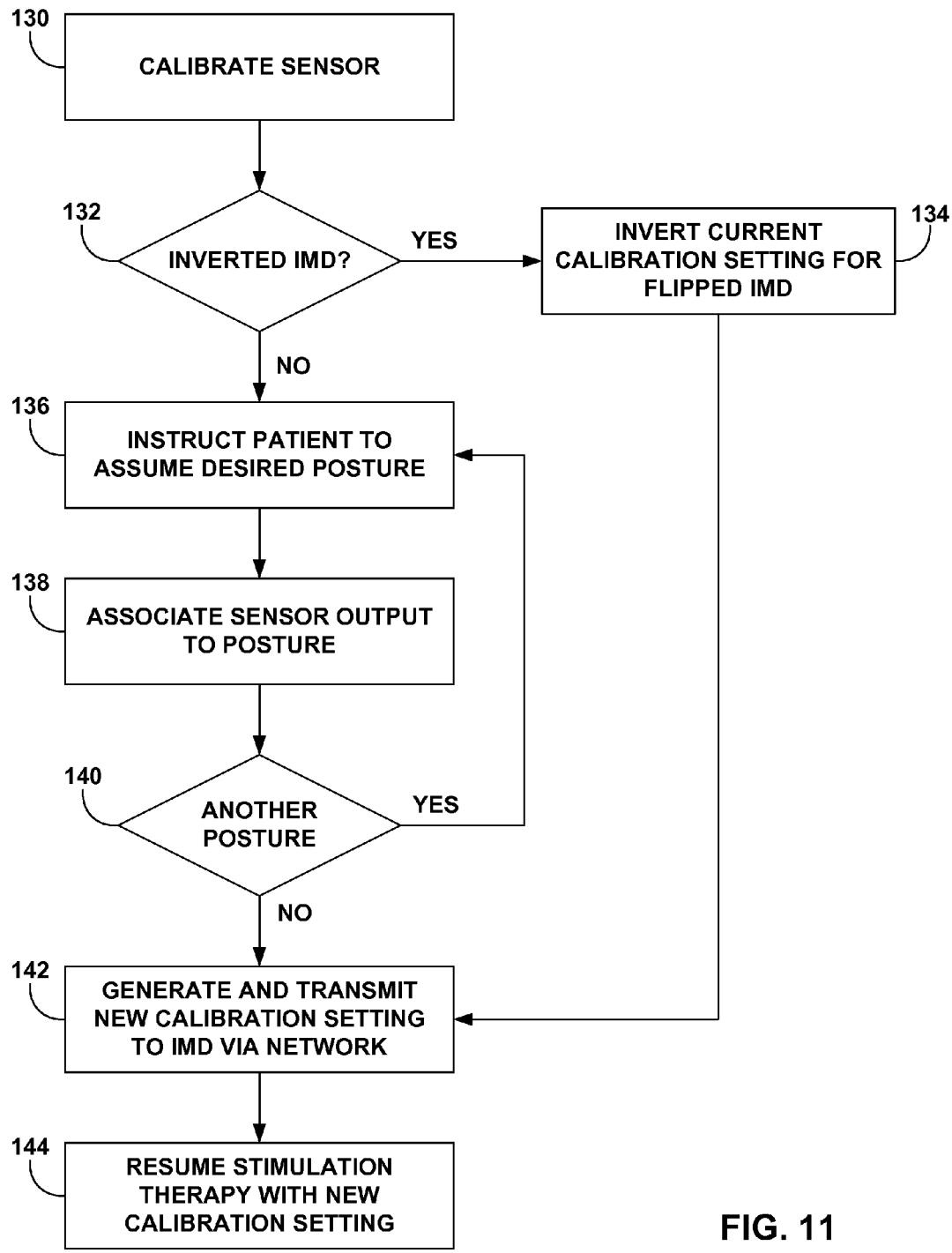
FIG. 11 is a flow diagram illustrating an example technique for using a remote networking device to calibrate a sensor of an IMD via a network.

FIG. 11 is a flow diagram illustrating an example technique for using a remote networking device 34 to calibrate sensor 51 of IMD 14 via network 32. As shown in FIG. 11, the clinician begins to calibrate sensor 51 of IMD 14 with remote networking device 34 (130). If the clinician, or remote networking device 34, identifies that the current calibration settings are inverted for IMD 14 (132), e.g., based on the received sensor information 36, the clinician may elect to simply invert the current calibration settings for IMD 14 flipped within patient 12 (134). If IMD 14 is not identified as inverted (132), the clinician may continue with full sensor 51 calibration.

The clinician instructs patient 12 to assume a desired activity, motion, or posture so that the output of sensor 51, received as sensor information 36 during calibration, may be matched to the patient activity, motion, or posture (136). The instruction may be delivered to patient 12 via external programmer 26, a computer, a webpage, a telephone, or any other communication device via network 32 or another communication medium. The clinician then associates the sensor output with the activity, motion, or posture (138). If there is another activity, motion, or posture for the calibration procedure (140), the clinician again instructs the patient to assume the next activity, motion, or posture y (136). If there are no more activities, the clinician generates the new calibration settings with the remote networking device 34 and transmits the new calibration settings to IMD 14 via network 32 (142). IMD 14 is then able to continue delivering therapy to patient 12 with the new calibration settings.

In some examples, the clinician may direct patient 12 to perform certain activities during the calibration procedure, but external programmer 26 or IMD 14 may generate the new calibration settings. Alternatively, the clinician may initiate the calibration procedure, but external programmer 26 and/or IMD 14 may independently perform the calibration procedure and generate the new calibration settings for sensor 51. In either case, calibration settings may be reviewed or confirmed by clinician prior to being used for therapy. In other examples, new calibration settings may be generated through interaction of patient 12 and the clinician with a webpage hosted by a server associated with network 32. In any event, the clinician may be able to provide new calibration settings to IMD 14 remotely instead of meeting patient 12 in person.

Figure 12:
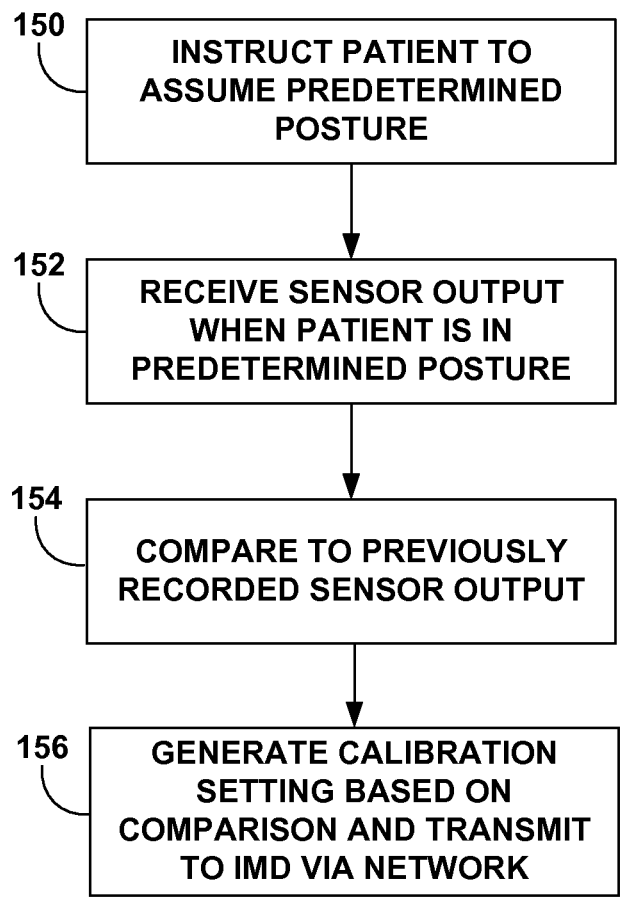
FIG. 12 is a flow diagram illustrating another example technique for using a remote networking device to calibrate a sensor of an IMD via a network.

FIG. 12 is a flow diagram illustrating another example technique for using a remote networking device to calibrate a sensor of an IMD via a network. Although calibration of sensor 51 is described in FIG. 11 with reference to embodiments in which multiple postures, motions, or activities may be associated the output of the sensor, the invention is not so limited. In the embodiment of FIG. 12, calibration involves directing the patient to assume a single predetermined posture, e.g., orientation relative to gravity, such as lying on his or her back, or standing upright (150).

The remote network device 34 may then receive the output of sensor 51 when the patient is within the predetermined posture (152). The remote networking device 34 compares the current output of the sensor with patient 12 in the predetermined posture to a previous output of the sensor when the patient previously assumed the predetermined posture, e.g., during initial programming and calibration of the IMD 14 (154). The remote networking device 34 may generate calibration settings based on the comparison, and transmit the calibration settings to IMD 14 (156). The calibration settings may take the form of one or more correction factors or values determined based on the comparison, which may be used by the IMD when controlling therapy or performing other functions based on the output of the sensor. For example, IMD 14 may adjust the output of sensor 51 by application of the correction factor or value to compensate for a change in the orientation of the sensor relative to the patient.

Various embodiments of the invention have been described. However, one skilled in the art will recognize that various modifications may be made to the described embodiments without departing from the scope of the invention. For example, the invention may be embodied as a computer-readable medium that includes instructions to cause a processor to perform any of the methods described herein.

Furthermore, as discussed above, in some embodiments remote networking device 34 may receive sensor information 36, determine whether sensor 51 requires calibration, and remotely calibrate the sensor with limited or no input from the clinician. Thus, remote networking device 34 may perform the techniques described above with reference to FIGS. 9-11 in a largely autonomous matter. In some embodiments, a clinician may be prompted to approve any new calibration settings identified through the automatic performance of such methods by remote networking device 34.

Additionally, although primarily described with reference to embodiments in which IMD 14 communicates with the remote networking device, the invention is not so limited. In other embodiments, programming device 26 may analyze sensor information for control of therapy delivered by IMD 14, and transmit sensor information to remote networking device if calibration is needed. Programming device 26 may perform any of the functions related to control or evaluation of therapy, or calibration of a sensor, described herein as being performed by an IMD. These and other embodiments are within the scope of the following claims.

The invention claimed is:

1. A method comprising:
receiving sensor information from an implantable medical device including an implantable accelerometer sensor at a remote networking device via a network, wherein the sensor information includes an output signal generated by the implantable accelerometer sensor that varies as a function of at least one of activity, motion, or posture of a patient, wherein the medical device is configured to determine the at least one of activity, motion, or posture of the patient using the signal generated by the implantable accelerometer sensor, wherein receipt of the output signal generated by the implantable accelerometer sensor indicates that a possible miscalibration has been identified;
presenting at least a portion of the received sensor information to a user via a user interface in response to receiving the sensor information;
subsequently receiving user input initiating calibration of the implantable accelerometer sensor; and
in response to the user input, calibrating the implantable accelerometer sensor via the remote networking device based on the output signal.

2. The method of claim 1, wherein calibrating the implantable accelerometer sensor comprises:
generating a new calibration setting for the implantable accelerometer sensor; and
transmitting the new calibration setting to at least one of the medical device or an external programmer for the medical device via the network.

3. The method of claim 1, wherein calibrating the implantable accelerometer sensor comprises:
determining that the implantable accelerometer sensor is inverted based on the output signal; and
inverting current calibration settings for the implantable accelerometer sensor based on the determination.

4. The method of claim 1, wherein calibrating the implantable accelerometer sensor comprises:
instructing the patient to assume a desired activity, motion, or posture; and
associating a value of the output signal generated by the implantable accelerometer sensor when the patient has assumed the desired activity, motion, or posture with the desired activity, motion, or posture.

5. The method of claim 1, wherein calibrating the implantable accelerometer sensor comprises:
instructing the patient to assume a predetermined posture;
receiving a value of the output signal generated by the implantable accelerometer sensor when the patient has assumed the predetermined posture;
comparing the received value to a previous value of the output signal when the patient previously assumed the predetermined posture; and
determining a calibration setting based on the comparison.

6. The method of claim 1, wherein calibrating the implantable accelerometer sensor comprises modifying at least one of a sensitivity, a length of hysteresis, or a degree of hysteresis of the implantable accelerometer sensor.

7. The method of claim 1, wherein calibrating the implantable accelerometer sensor comprises receiving new calibration settings at the remote networking device from a clinician.

8. The method of claim 1, further comprising determining the at least one of activity, motion, or posture of the patient based on the output signal generated by the implantable accelerometer sensor.

9. The method of claim 8, further comprising controlling the delivery of therapy to the patient from the medical device based on the determined at least one of activity, motion, or posture of the patient.

10. The method of claim 1, wherein the medical device is configured to determine the patient occupies at least one of an upright posture, reclining posture, or lying posture using the output signal generated by the implantable accelerometer sensor.

11. A remote networking device comprising:
a communications circuit that receives sensor information from an implantable medical device including an implantable accelerometer sensor via a network, wherein the sensor information includes an output signal generated by the implantable accelerometer sensor that varies as a function of at least one of activity, motion, or posture of a patient, wherein the medical device is configured to determine the at least one of activity, motion, or posture of the patient based on the output signal generated by the implantable accelerometer sensor, and wherein receipt of the output signal generated by the implantable accelerometer sensor indicates that a possible miscalibration has been identified; and
a processor that, in response to receiving the output signal, presents at least a portion of the received sensor information to a user via a user interface in response to receiving the sensor information, subsequently receives user input initiating calibration of the implantable accelerometer sensor, an in response to the user input, calibrates the sensor via the network based on the output signal.

12. The remote networking device of claim 11, wherein:
the processor generates a new calibration setting for the implantable accelerometer sensor; and
the communications circuit transmits the new calibration setting to at least one of the medical device or an external programmer for the medical device via the network.

13. The remote networking device of claim 11, wherein the processor determines that the implantable accelerometer sensor is inverted based on the signal, and inverts a current calibration setting for the implantable accelerometer sensor based on the determination.

14. The remote networking device of claim 11, wherein the processor calibrates the implantable accelerometer sensor by associating a value of the output signal generated by the implantable accelerometer sensor when the patient assumes an activity, motion, or posture with the activity, motion, or posture.

15. The remote networking device of claim 11, wherein:
the communications circuit receives a value of the output signal generated by the implantable accelerometer sensor with the patient in a predetermined posture; and
the processor compares the received value to a previous value of the output signal when the patient was previously in the predetermined posture, and determines a calibration setting based on the comparison.

16. The remote networking device of claim 11, wherein the processor modifies at least one of a sensitivity, a length of hysteresis, or a degree of hysteresis of the implantable accelerometer sensor to calibrate the sensor.

17. The remote networking device of claim 11, wherein:
the processor receives new calibration settings from a clinician; and
the communications circuit transmits the new calibration setting to at least one of the implantable medical device or an external programmer for the implantable medical device via the network.

18. The remote networking device of claim 11, wherein the medical device is configured to control the delivery of therapy to the patient from the medical device based on the determined at least one of activity, motion, or posture of the patient.

19. The remote networking device of claim 11, wherein the medical device is configured to determine the patient occupies at least one of an upright posture, reclining posture, or lying posture using the output signal generated by the implantable accelerometer sensor.

20. A method comprising:
identifying possible miscalibration of an implantable accelerometer sensor of a medical device based on at least one of an output signal generated by the implantable accelerometer sensor or received patient input, wherein the output signal generated by the implantable accelerometer sensor varies as a function of at least one of activity, motion, or posture of a patient, wherein the medical device is configured to determine the at least one of activity, motion, or posture of the patient based on the output signal generated by the implantable accelerometer sensor;
transmitting sensor information from the implantable medical device to a remote networking device via a network in response to the identification, wherein the sensor information includes the output signal generated by the implantable accelerometer sensor, wherein transmission of the output signal generated by the implantable accelerometer sensor to the remote networking device indicates that the possible miscalibration has been identified; and
receiving a calibration setting for the implantable accelerometer sensor from the remote networking device via the network in response to the sensor information.

21. The method of claim 20, wherein identifying possible miscalibration of the implantable accelerometer sensor comprises identifying inappropriate therapy delivered to the patient based on the output signal.

22. The method of claim 20, wherein identifying possible miscalibration of the implantable accelerometer sensor comprises identifying an unexpected value of the output signal.

23. The method of claim 20, further comprising:
applying the calibration setting to adjust a value of the output signal generated by the implantable accelerometer sensor; and
at least one of controlling delivery of therapy to the patient or monitoring the patient based on the adjusted value.

24. The method of claim 20, further comprising determining the at least one of activity, motion, or posture of the patient based on the output signal generated by the implantable accelerometer sensor.

25. The method of claim 24, further comprising controlling the delivery of therapy to the patient from the medical device based on the determined at least one of activity, motion, or posture of the patient.

26. The method of claim 20, wherein the medical device is configured to determine the patient occupies at least one of an upright posture, reclining posture, or lying posture using the output signal generated by the implantable accelerometer sensor.

27. A device comprising:
a communications circuit; and
a processor that identifies possible miscalibration of an implantable accelerometer sensor of a medical device based on at least one of an output signal generated by the implantable accelerometer sensor or received patient input, wherein the output signal generated by the implantable accelerometer sensor varies as a function of at least one of activity, motion, or posture of a patient, wherein the medical device is configured to determine the at least one of activity, motion, or posture of the patient based on the output signal generated by the implantable accelerometer sensor, transmits sensor information from the implantable medical device to a remote networking device via the communications circuit and a network in response to the identification, wherein the sensor information includes the output signal generated by the implantable accelerometer sensor, wherein transmission of the output signal generated by the implantable accelerometer sensor to the remote networking device indicates that the possible miscalibration has been identified, and receives a calibration setting for the implantable accelerometer sensor from the remote networking device via the communications circuit and the network in response to the sensor information.

28. The device of claim 27, wherein the processor identifies inappropriate therapy delivered to the patient based on the output signal, and transmits the output signal in response to the identification.

29. The device of claim 27, wherein the processor identifies an unexpected value of the output signal, and transmits the output signal in response to the identification.

30. The device of claim 27, wherein the processor applies the calibration setting to adjust a value of the output signal generated by the implantable accelerometer sensor, and at least one of controls delivery of therapy to the patient or monitors the patient based on the adjusted value.

31. The device of claim 27, wherein the device comprises one of an implantable medical device that comprises the implantable accelerometer sensor or an external programmer for the medical device.

32. The device of claim 27, wherein the medical device is configured to control the delivery of therapy to the patient from the medical device based on the determined at least one of activity, motion, or posture of the patient.

33. The device of claim 27, wherein the medical device is configured to determine the patient occupies at least one of an upright posture, reclining posture, or lying posture using the output signal generated by the implantable accelerometer sensor.

34. A system comprising:
a local device that identifies possible miscalibration of an implantable accelerometer sensor of a medical device based on at least one of an output signal generated by the implantable accelerometer sensor or received patient input, wherein the output signal generated by the implantable accelerometer sensor varies as a function of at least one of activity, motion, or posture of a patient, wherein the medical device is configured to determine the at least one of activity, motion, or posture of the patient based on the output signal generated by the implantable accelerometer sensor, transmits sensor information including the output signal generated by the implantable accelerometer sensor from the implantable medical device to a remote networking device via a network in response to the identification, and receives a calibration setting for the implantable accelerometer sensor in response to the output signal; and
the remote networking device that communicates with the local device via the network, wherein the remote networking device receives the output signal from the local device via the network, wherein receipt of the output signal generated by the implantable accelerometer sensor indicates that the possible miscalibration has been identified, presents at least a portion of the received sensor information to a user via a user interface in response to receiving the sensor information, subsequently receives user input initiating calibration of the implantable accelerometer sensor, and calibrates the implantable accelerometer sensor via the remote networking device based on the output signal.

35. The system of claim 34, wherein the local device comprises one of the medical device that comprises the sensor or an external programmer for the medical device.

36. The system of claim 34, further comprising the medical device configured to determine the at least one of the activity, motion, or posture of the based on the output signal generated by the implantable accelerometer sensor.

37. The system of claim 36, wherein the medical device is configured to control the delivery of therapy to the patient based on the determined at least one of activity, motion, or posture of the patient.

38. The system of claim 34, wherein the medical device is configured to determine the patient occupies at least one of an upright posture, reclining posture, or lying posture using the output signal generated by the implantable accelerometer sensor.

* * * * *

UNITED STATES PATENT AND TRADEMARK OFFICE
CERTIFICATE OF CORRECTION

PATENT NO.        : 9,723,987 B2                                    Page 1 of 1
APPLICATION NO.   : 12/738047
DATED             : August 8, 2017
INVENTOR(S)       : Steven M. Goetz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 692 days.

Signed and Sealed this
Twenty-fifth Day of September, 2018

Andrei Iancu
*Director of the United States Patent and Trademark Office*